United States Patent [19]

Guthrie et al.

[11] Patent Number: 5,292,651
[45] Date of Patent: Mar. 8, 1994

[54] METHOD FOR CLONING AND PRODUCING THE NAEI RESTRICTION ENDONUCLEASE AND METHYLASE

[75] Inventors: Ellen P. Guthrie, Andover; Elizabeth M. Van Cott, Malden; Christopher H. Taron, Marblehead, all of Mass.

[73] Assignee: New England Biolabs, Inc., Beverly, Mass.

[21] Appl. No.: 880,913

[22] Filed: May 12, 1992

[51] Int. Cl.$^5$ .................. C12N 9/22; C12N 15/55
[52] U.S. Cl. .................. 435/199; 435/320.1; 435/252.33; 435/252.35; 435/193; 536/23.2
[58] Field of Search .......... 435/199, 193, 320.1, 435/252.33, 252.35; 536/27, 23.2

[56] References Cited

FOREIGN PATENT DOCUMENTS 0193413 9/1986 European Pat. Off. ...... C12N 15/00

OTHER PUBLICATIONS

Wilson, G. G. (1991) Nuc. Acids Res. 19(10), 2539, 2540, 2552, 2563–2566.
Wilson, G. G. (1988) Gene 74, 281–289.
Lunnen, K. D., et al., (1988) Gene 74, 25–32.
V. Kosykh et al., Molec. Gen. Genet., 178:717–718 (1980).
M. Mann et al., Gene, 3:97–112 (1978).
R. Walder et al., Proc. Natl. Acad. Sci. U.S.A., 78:1503–1507 (1981).
L. Bougueleret et al. Nucleic Acids Research, 12:3659–3676 (1984).
T. Gingeras et al., Proc. Natl. Acad. Sci. U.S.A., 80:402–406 (1983).
G. Theriault et al., Gene, 19:355–359 (1982).
R. Blumenthal et al., J. Bacteriol., 164:501–509 (1985).
E. Szomolanyi et al., Gene, 10:219–225 (1980).
A. Janulaitis et al., Gene, 20:197–204 (1982).
A. Kiss et al., Gene, 21:111–119 (1983).
R. Walder et al., J. Biol. Chem., 258:1235–1241 (1983).
E. Raleigh et al., Proc. Natl. Acad. Sci. U.S.A., 83:9070–9074 (1986).
A. Piekarowicz et al., Nucleic Acids Research, 19:1831–1835 (1991).
M. Conrad et al., Proc. Natl. Acad. Sci. U.S.A. 86:9707–9711 (1989).
J. Shine et al., Proc. Natl. Acad. Sci. U.S.A., 71:1342–1346 (1974).
J. M. Ward et al., Mol. Gen. Genet., 203:468–478 (1986).
H. Birnboim et al., Nucleic Acids Research, 7:1513–1523 (1979).
E. Southern et al., J. Mol. Biol. 98:503–517 (1975).
E. Van Cott et al., Gene, 74:55–59 (1988).

Primary Examiner—Charles L. Patterson, Jr.
Attorney, Agent, or Firm—David G. Conlin; Gregory D. Williams

[57] ABSTRACT

The present invention is directed to a method for cloning and producing the NaeI restriction endonuclease by 1) introducing the restriction endonuclease gene from *Nocardia aerocolonigenes* into a host whereby the restriction gene is expressed; 2) fermenting the host which contains the plasmid encoding and expressing the NaeI restriction endonuclease activity, and 3) purifying the NaeI restriction endonuclease from the fermented host which contains the plasmid encoding and expressing the NaeI restriction endonuclease activity.

7 Claims, 7 Drawing Sheets

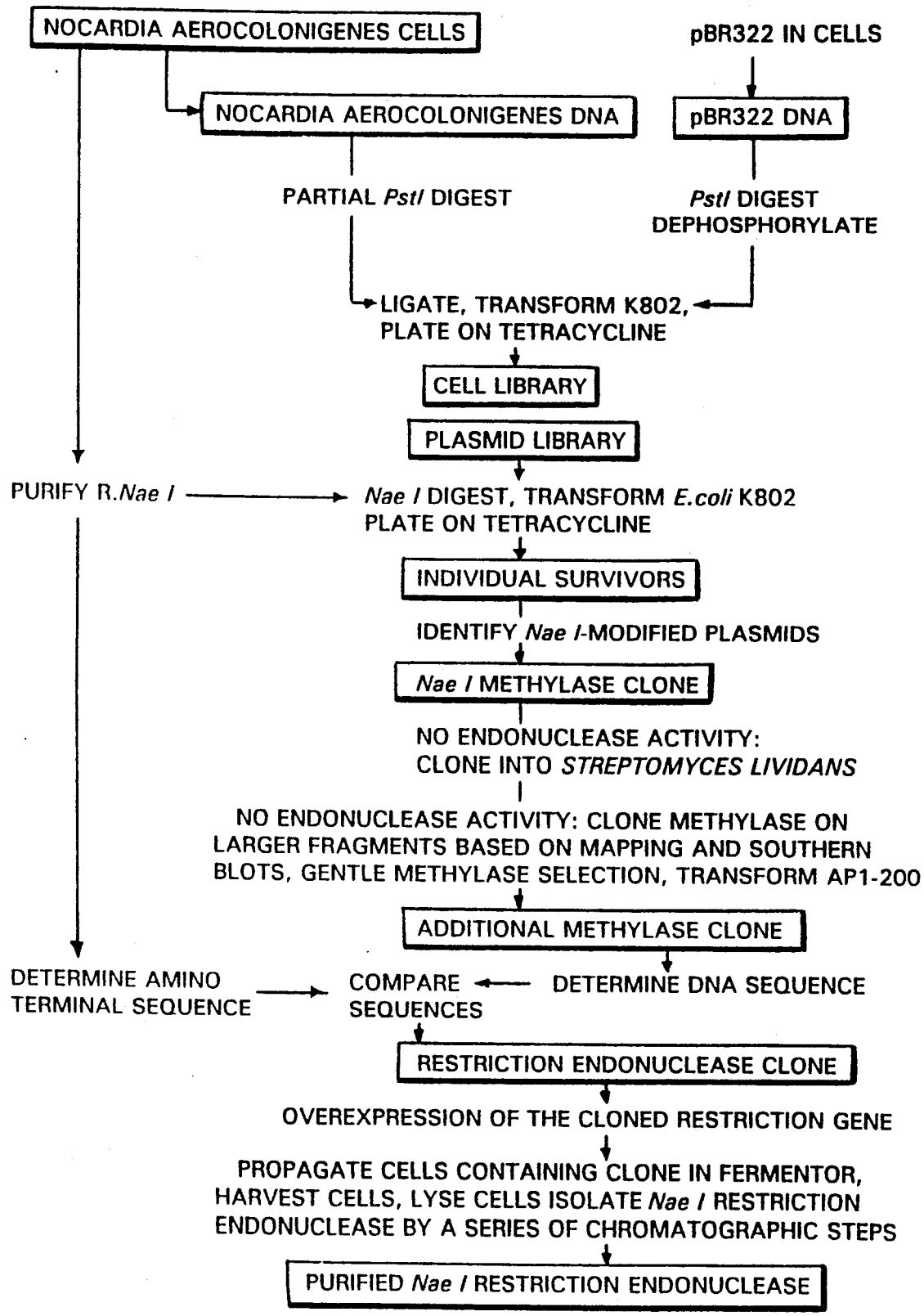
FIG. IA

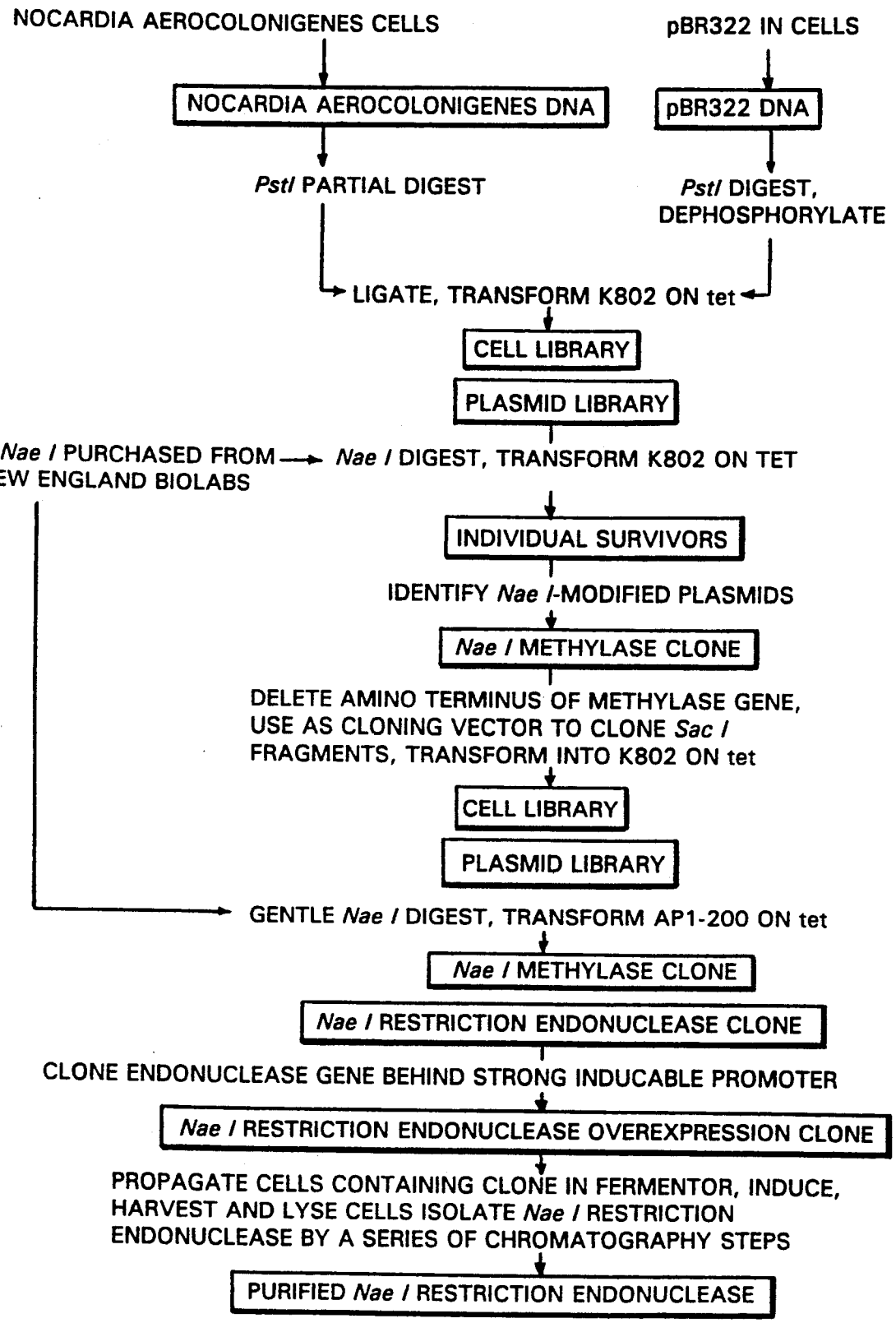
FIG. IB

METHOD FOR CLONING AND PRODUCING THE NAEI RESTRICTION ENDONUCLEASE AND METHYLASE

BACKGROUND OF THE INVENTION

The present invention relates to recombinant DNA which encodes the NaeI restriction endonuclease and modification methylase, and the production of these enzymes from the recombinant DNA.

Restriction endonucleases are a class of enzymes that occur naturally in bacteria. When they are purified away from other contaminating bacterial components, restriction endonucleases can be used in the laboratory to cut DNA molecules into precise fragments. This property enables DNA molecules to be uniquely identified and to be fractionated into their constituent genes. Restriction endonucleases have proved to be indispensable tools in modern genetic research. They are the biochemical 'scissors' by means of which genetic engineering and analysis is performed.

Restriction endonucleases act by recognizing and binding to particular sequences of nucleotides (the 'recognition sequence') along the DNA molecule. Once bound, they cleave the molecule within, or to one side of, the recognition sequence. Different restriction endonucleases have affinity for different recognition sequences. Close to one hundred different restriction endonucleases have been identified among the many hundreds of bacterial species that have been examined to date.

Bacteria tend to possess at most, only a small number restriction endonucleases per species. The endonucleases typically are named according to the bacteria from which they are derived. Thus, the species *Haemophilus aegyptius* for example, synthesizes three different restriction endonucleases, named HaeI, HaeII and HaeIII. These enzymes recognize and cleave the sequences (AT)GGCC(AT),PuGCGCPy and GGCC respectively. *Escherichia coli* RY13, on the other hand, synthesizes only one enzyme, EcoRI, which recognizes the sequence GAATTC.

While not wishing to be bound by theory, it is thought that in nature, restriction endonucleases play a protective role in the welfare of the bacterial cell. They enable bacteria to resist infection by foreign DNA molecules like viruses and plasmids that would otherwise destroy or parasitize them. They impart resistance by scanning the lengths of the infecting DNA molecule and cleaving them each time that the recognition sequence occurs. The cleavage that takes place disables many of the infecting genes and renders the DNA susceptible to further degradation by non-specific endonucleases.

A second component of bacterial protective systems are the modification methylases. These enzymes are complementary to restriction endonucleases and they provide the means by which bacteria are able to protect their own DNA and distinguish it from foreign, infecting DNA. Modification methylases recognize and bind to the same nucleotide recognition sequence as the corresponding restriction endonuclease, but instead of cleaving the DNA, they chemically modify one or other of the nucleotides within the sequence by the addition of a methyl group. Following methylation, the recognition sequence is no longer bound or cleaved by the restriction endonuclease. The DNA of a bacterial cell is always fully modified by virtue of the activity of its modification methylase. It is therefore completely insensitive to the presence of the endogenous restriction endonuclease. It is only unmodified, and therefore identifiably foreign DNA, that is sensitive to restriction endonuclease recognition and attack.

With the advent of genetic engineering technology, it is now possible to clone genes and to produce the proteins and enzymes that they encode in greater quantities than are obtainable by conventional purification techniques. The key to isolating clones of restriction endonuclease genes is to develop a simple and reliable method to identify such clones within complex 'libraries', i.e. populations of clones derived by 'shotgun' procedures, when they occur at frequencies as low as $10^{-3}$ to $10^{-4}$. Preferably, the method should be selective, such that the unwanted majority of clones are destroyed while the desirable rare clones survive.

Type II restriction-modification systems are being cloned with increasing frequency. The first cloned systems used bacteriophage infection as a means of identifying or selecting restriction endonuclease clones (EcoRII: Kosykh et al., Molec. gen. Genet 178: 717-719, (1980); HhaII: Mann et al., Gene 3: 97-112, (1978); PstI: Walder et al., Proc. Nat. Acad. Sci. 78 1503-1507, (1981)). Since the presence of restriction- modification systems in bacteria enable them to resist infection by bacteriophages, cells that carry cloned restriction-modification genes can, in principle, be selectively isolated as survivors from libraries that have been exposed to phage. This method has been found, however, to have only limited value. Specifically, it has been found that cloned restriction-modification genes do not always manifest sufficient phage resistance to confer selective survival.

Another cloning approach involves transferring systems initially characterized as plasmid-borne into *E. coli* cloning plasmids (EcoRV: Bougueleret et al., Nucl. Acid. Res. 12: 3659-3676, (1984); PaeR7: Gingeras and Brooks, Proc. Natl. Acad. Sci. USA 80: 402-406, (1983); Theriault and Roy, Gene 19: 355-359 (1982); PvuII: Blumenthal et al., J. Bacteriol. 164: 501-509, (1985)).

A third approach, and one that is being used to clone a growing number of systems are now being cloned by selection for an active methylase gene (see, e.g., EPO No.: 193,413 published Sep. 3, 1986. Since restriction and modification genes are often closely linked, both genes can often be cloned simultaneously. This selection does not always yield a complete restriction system however, but instead yields only the methylase gene (BspRI: Szomolanyi et al., Gene 10: 219-225, (1980); Bcn I: Janulaitis et al, Gene 20: 197-204 (1982); Bsu RI: Kiss and Baldauf, Gene 21: 111-119, (1983); and Msp I: Walder et al., J. Biol. Chem. 258: 1235-1241, (1983)).

In some systems the cloning problem may lie in trying to introduce the endonuclease gene into a host not already protected by modification. If the methylase gene and endonuclease gene are introduced on a common DNA fragment, the methylase gene must modify or protect the host before the endonuclease gene cleaves the host's genome.

Another obstacle to cloning these systems in *E. coli* was discovered in the process of cloning diverse methylases. Many *E. coli* strains (including those normally used in cloning) have systems that resist the introduction of DNA containing cytosine methylation. (Raleigh and Wilson, Proc. Natl. Acad. Sci., USA 83: 9070-9074, (1986)). Therefore, it is also necessary to carefully consider which E. coli strain(s) to use for cloning.

Because purified restriction endonucleases, and to a lesser extent, modification methylases, are useful tools for characterizing and rearranging DNA in the laboratory, there is a commercial incentive to obtain strains of bacteria through recombinant DNA techniques that synthesize these enzymes in abundance. Such strains would be useful because they would simplify the task of purification as well as providing the means for production in commercially useful amounts.

SUMMARY OF THE INVENTION

The present invention relates to recombinant DNA e*coding the genes for the NaeI restriction endonuclease and modification methylase obtainable from *Nocardia aerocolonigenes* (ATCC 23870) as well as related methods for the production of these enzymes from the recombinant DNA. This invention also relates to a transformed host which expresses the restriction endonuclease NaeI, an enzyme which recognizes the DNA sequence 5'-GCCGGC-3' and cleaves in the middle of the recognition sequence after the second C leaving no overhang (Wilson, G., D. Comb, L. Greenough, and I. Schildkraut, unpublished observations). NaeI methylase or restriction endonuclease produced in accordance with the present invention is substantially pure and free of the contaminants normally found in restriction endonuclease preparations made by conventional techniques as described in step 18 of example 1. One preferred method for cloning the NaeI restriction-modification system comprises: selecting an appropriate vector, forming several libraries containing DNA from *Nocardia aerocolonigenes*, isolating those clones which contain DNA coding for the NaeI modification methylase, determining that the endonuclease gene was not present by assaying for endonuclease activity in strains of E. coli and of *Streptomyces lividans* containing the methylase clone, cloning the chromosomal DNA adjacent to the methylase gene using a vector with a portion of the methylase gene deleted, a modified selection protocol, and, as a host, E. coli AP1-200 (Piekarowicz et al.) to screen for those clones, determining that there was no detectable endonuclease activity produced by the new clone, attempting to clone this DNA into *Streptomyces lividans* looking for NaeI restriction endonuclease expression, sequencing the newly cloned DNA and the amino terminus of the NaeI restriction endonuclease, and localizing the endonuclease gene on the newly cloned DNA fragment by comparing these sequences.

BRIEF DESCRIPTION OF THE DRAWINGS

FIGS. 1A and 1B: Scheme for cloning and producing the NaeI restriction endonuclease:

FIG. 1A illustrates the procedures for determining the preferred method for cloning and producing the NaeI restriction endonuclease.

FIG. 1B illustrates the preferred method for cloning and producing the NaeI restriction endonuclease based on actual results presented in FIG. 1A: At the onset of the cloning project, it was not known which endonucleases or conditions would be successful in cloning the NaeI restriction-modification system, nor where the restriction and modification genes were located within such clones. The cloning results and subsequent DNA sequencing, mapping, and characterization of the clones described in FIG. 1A and example 1 reveal the previously unknown direct pathway for cloning and expressing the NaeI restriction-modification system.

DETAILED DESCRIPTION OF THE INVENTION

The present invention relates to recombinant DNA which encodes the NaeI restriction endonuclease and modification methylase, as well as to the enzymes produced from such a recombinant DNA.

The cloning of the NaeI restriction-modification genes from *Nocardia aerocolonigenes* into E. coli proved to be unusually difficult due to a combination of two factors. First, unlike many other restriction-modification systems, NaeI genes do not express well in E. coli. In accordance with the present invention, it has been found that obtaining methylase clones by methylase selection is not successful unless the methylase gene is cloned on a small enough fragment such that the start of the gene is close enough to and aligned with a promoter on the cloning vector. In such cases, the methylase gene is expressed and the clone is able to survive methylase selection (the identification of methylase clones by their ability to resist and survive NaeI digestion). Second, the orientation of the NaeI endonuclease gene with respect to the methylase gene is such that the genes can not be cloned together in E. coli under control of a single promoter. Since the endonuclease gene is first followed by the methylase gene with both genes reading in the same direction (FIG. 4), if these genes were cloned together behind a strong promoter, the endonuclease gene would be in a position closer to the promoter than the methylase gene and would be more strongly expressed than the methylase gene resulting in a clone which is nonviable. In accordance with the present invention, both genes can be cloned together, as in pEVnaeIRM9.3 (FIG. 3), but only if they are far enough away from a promoter in the vector to not get expression from that promoter. Alternatively, the genes can be cloned separately under the control of separate promoters.

In the majority of cloning attempts it was found that the fragment encoding the methylase was too large and/or was in the wrong orientation and the methylase gene was not expressed. It is believed that the clones were not modified, and therefore destroyed by the selection that was designed to isolate them. In accordance with the present invention, the NaeI methylase gene was cloned by constructing and analyzing several libraries until one was found that carried a fragment encoding the methylase gene, without the intact endonuclease gene, in the correct orientation and close enough to a plasmid promoter to get methylase expression. While 4 different restriction endonucleases were used to both partially cut and fully cut DNA to construct 9 different libraries, only a partial PstI library was found to carry a clone with the methylase gene on such a fragment. At the onset of the cloning project, it was not known which endonuclease was the most likely to succeed.

Figure 2:
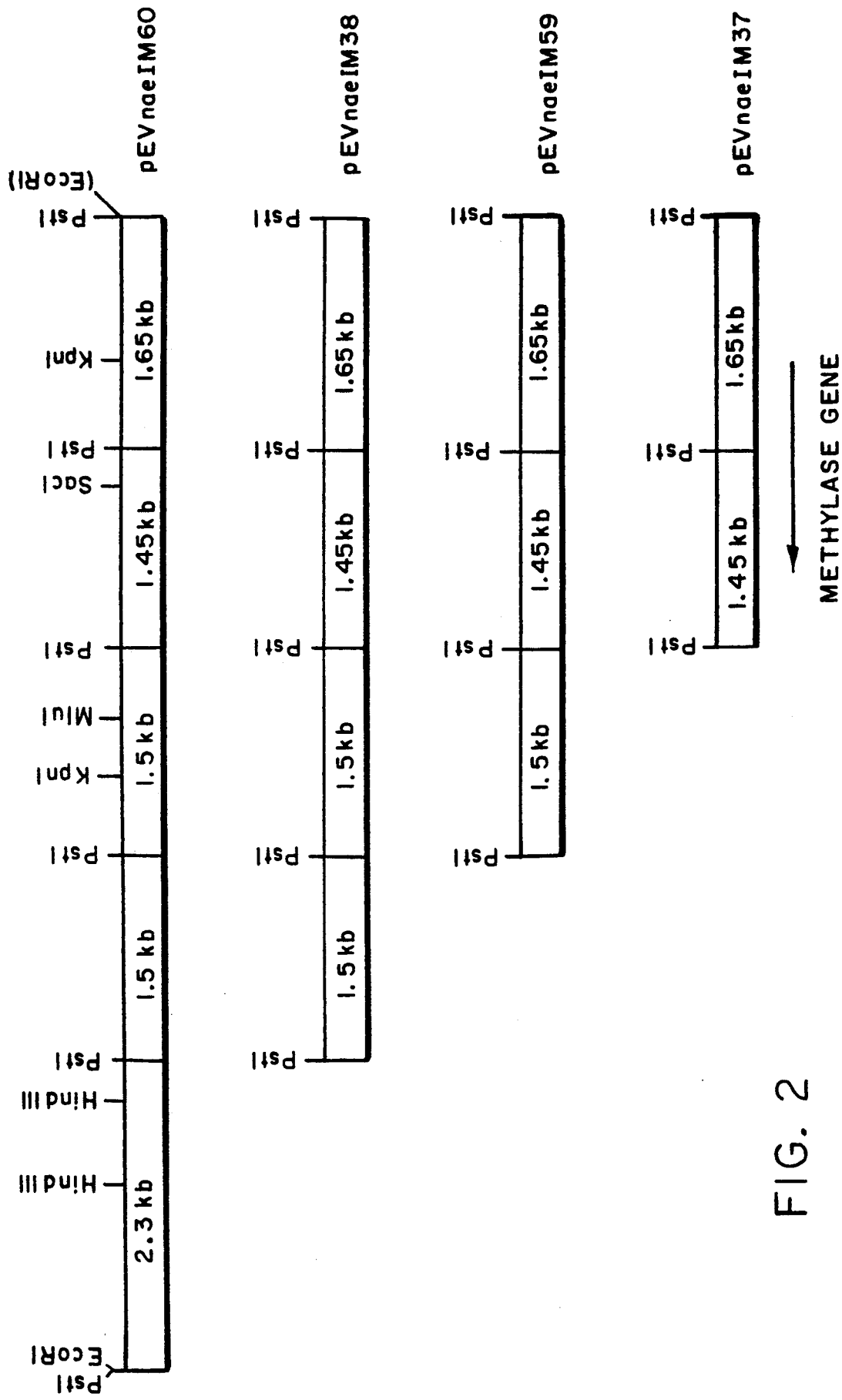
FIG. 2 is a map of several of the PstI partial clones obtained from the methylase selection of the PstI library.

Of the nineteen methylase clones obtained after selection of a partial PstI library, all carried a least two identical PstI fragments. Eighteen were in the same orientation in the vector. These eighteen clones were completely methylated. Several of the clones had additional PstI fragments which mapped to one side of the clone (FIG. 2). None of these clones, as was determined later, contained the intact endonuclease gene.

Figure 3:
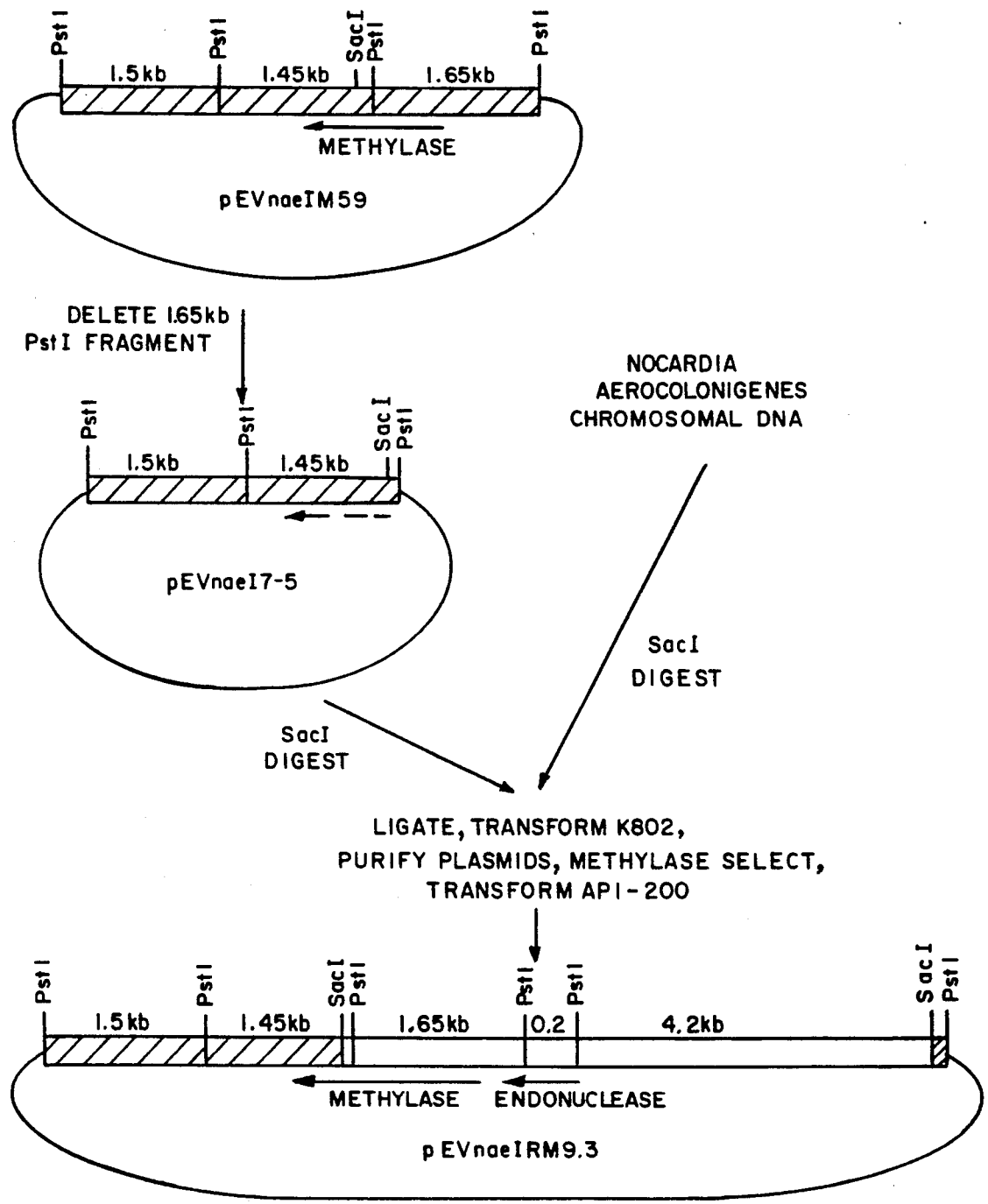
FIG. 3 is a schematic diagram of the construction of pEVnaeI7-5 and the subsequent cloning of pEVnaeIRM9.3.

The cloning of the endonuclease gene was problematic. It was first determined by Southern analysis that a SacI fragment containing a portion of the methylase gene could possibly contain enough flanking DNA to the right of the methylase gene to encode for the entire endonuclease gene, depending on the size of the endonuclease gene and the exact location of the methylase gene. However, cloning just the SacI fragment alone would not have resulted in viable clones, since the endonuclease gene would have been cloned without an intact methylase gene. The problem arose in how to clone the endonuclease gene while keeping the methylase gene intact, so that it could afford protection to the host from cleavage by the endonuclease. In addition, the vector must have NaeI sites which are able to be cut with NaeI, since NaeI has marked site preferences, i.e.) NaeI cuts some sites preferentially to other sites [Conrad and Topal, Proc. Natl. Acad. Sci. USA 86: 9707-9711, (1989)]. In accordance with the present invention this was resolved by deleting one PstI fragment from pEVnaeIM-59, removing the right half of the methylase gene (FIG. 3). The resulting plasmid, pEVnaeI7-5, has a single SacI site, several NaeI sites for selection, and a portion of the NaeI methylase which could be reconstructed if the remainder of the methylase gene were cloned adjacent to it resulting in an intact NaeI methylase gene and methylase protection. Normal methylase selection of a SacI library constructed in this vector yielded no clones. Assuming that this result was due to the distance of the methylase gene from the ampicillin promoter in the vector, an attempt was made to do a less stringent methylase selection and to use *E. coli* AP1-200 as the host. This strain allowed for the screening of active, but weakly expressing, methylase clones. One clone, pEVnaeIRM9.3, was isolated which gave partial methylase protection to the vector. This clone was shown by restriction digestion analysis to contain DNA to the right of the methylase gene. This clone showed no detectable levels of NaeI endonuclease in *E. coli*.

Expression of the NaeI restriction endonuclease gene was found to be an even greater problem. Methylase clones from many other restriction-modification systems can be screened for restriction endonuclease activity by an in vitro assay. However, pEVnaeIRM9.3 in *E. coli* showed no detectable NaeI endonuclease activity by an in vitro assay. Past experience with restriction-modification systems from Nocardia and Streptomyces has shown that it is often difficult to detect restriction endonuclease activity from these systems when cloned in *E. coli*. However, restriction endonuclease gene expression can often be detected when the restriction-modification genes are cloned into a more closely related host such as *Streptomyces lividans*. In order to determine if the intact restriction endonuclease gene was cloned on pEVnaeIRM9.3, several attempts were made to try to subclone the insert from pEVnaeIRM9.3 into *Streptomyces lividans*. However, all attempts failed, probably due to the endonuclease being expressed at higher levels than the methylase gene. Not until the methylase gene was cloned separately on a low copy Streptomyces vector in *Streptomyces lividans*, and the endonuclease gene was cloned subsequently into this preprotected strain on a high copy vector, could NaeI endonuclease activity be detected. In order to locate the exact position of the NaeI restriction endonuclease gene on the clone pEVnaeIRM9.3, the DNA was sequenced, the sequence of the amino-terminus of the restriction endonuclease protein was determined from a purer preparation of NaeI from *Nocardia aerocolonigenes*, and the DNA sequence of the clones was compared to the sequence of the amino-terminus of the endonuclease. Once the start of the endonuclease gene was located, the best strategy for overexpressing the NaeI restriction endonuclease gene was determined (discussed in more detail below).

The method described herein by which the NaeI restriction gene and methylase gene are preferably cloned and expressed is illustrated in FIGS. 1A and 1B and includes the following steps:

1. The DNA of *Nocardia aerocolonigenes* is purified.

2. The DNA is digested completely and/or partially with a restriction endonuclease such as PstI, or any of its isoschizomers, that cleaves the entire NaeI methylase gene into a fragment(s) that carries the start of the gene close to one end of the fragment(s) without containing the intact endonuclease gene. The fragment(s) should also be of cloneable size, that is, about 1.5-13 kb. It was found that other endonucleases that were tried did not satisfy the conditions described above including BamHI, BclI, BglII, EcoRI, HindII, NsiI, PvuII, Sau3A, and XhoII.

3. pBR322 (or any other vector which has the same tetracycline resistance gene found in pBR322) was chosen as the cloning vector since it contains four NaeI sites, two of which are readily cleaved, one site is cleaved moderately slowly, and the fourth is cleaved 50-fold more slowly by the NaeI restriction endonuclease. This is unlike some other vectors, such as the λ-based vectors, which have an NaeI site which is not cleaved by the NaeI endonuclease.

4. The digested DNA's are ligated to the cloning vector. The resulting mixtures are used to transform an appropriate host, i.e. a hsdR−, mcrBC-strain, such as *E. coli* strain RR1 or K802 cells (ATCC 31343 and ATCC 33526, respectively). The present study found that K802 is the preferred host cell.

5. The DNA/cell mixtures are preferably plated on antibiotic media selective for transformed cells, such as ampicillin or tetracycline. After incubation, the transformed cell colonies are harvested together to form the primary cell libraries. As described above, a total of 9 such primary cell libraries were ultimately constructed using different combinations of cloning endonucleases, complete or partial digestion of the Nocardia DNA by the respective cloning endonuclease, and host strains.

6. The recombinant plasmids are purified in toto from the primary cell libraries to make primary plasmid libraries.

7. The purified plasmid libraries are then digested to completion in vitro with the NaeI restriction endonuclease which is prepared from *Nocardia aerocolonigenes* cells, or any NaeI isoschizomer such as NgoMI. NaeI restriction endonuclease digestion causes the selective destruction of unmodified, non-methylase-containing clones, resulting in an increase in the relative frequency of NaeI methylase-carrying clones. Exonuclease and/or phosphatase may also be added to the digestion to enhance the destruction of non-methylase clones.

9. Identification of NaeI methylase clones: The digested plasmid library DNA's are transformed back into a convenient host such as *E. coli* strain RR1 or K802, and transformed colonies are again obtained by plating on antibiotic plates. The colonies are picked and their DNA is analyzed for the presence of the NaeI modification gene in the following manner: The plasmid DNA that they carry is purified and incubated in vitro with NaeI restriction endonuclease to determine whether it is resistant to digestion by NaeI.

10. Once it has been established that the methylase gene has been cloned, the clone is assayed for NaeI restriction endonuclease activity. If activity is detected, then the NaeI restriction gene is linked to the methylase gene and is present in the clone. In such a case one could then skip to step 13 below. However, in accordance with the present invention, it has been found that even if present, the restriction gene is not expressed. The lack of restriction activity indicates that the restriction gene is not linked to the methylase gene, or it is linked but not cloned intact with the methylase gene, or it is cloned intact but not expressed. In order to determine which of the above three possibilities is the true situation, the cloned fragment is restriction-mapped and deletions are made to determine where the relative position of the methylase gene is within the cloned fragment. The information is then used to determine if there is enough DNA on either side of the methylase gene to encode a restriction gene, if it were linked. If there is enough room, the restriction gene is assumed not to be linked, or to be present in the clone but not expressed (skip to step 12). If there is not enough room on both sides of the methylase gene in the cloned DNA to encode a linked restriction gene, as was found for the PstI clone, pEVnaeIM38, of the present invention, a portion of the methylase gene is used to probe digests of the *Nocardia aerocolonigenes* chromosome to generate by Southern hybridization a genomic map of the region extending beyond the boundaries of the existing cloned DNA. This data helps identify certain endonucleases that cleave the restriction-modification region into individual fragments that carry the methylase gene as well as larger amounts of adjacent DNA. The exact sizes of the fragments generated by such endonucleases are calculated from the data as well. Presumably, if the restriction and modification genes are found to be linked, such fragments would also encode the restriction gene.

11. Enriched libraries are constructed by gel-purifying the fragments described in step 10 and ligating them into an appropriate vector such as pEVnaeI7-5 (a derivative of pBR322, the construction of which is described in example 1, step 14). Clones carrying DNA to the right of the methylase gene can be isolated by a gentle methylase selection and/or by screening for methylase activity using *E. coli* AP1-200.

12. Identification of restriction gene clones: In accordance with the present invention, it has been found that clones carrying the NaeI restriction endonuclease gene cannot be identified by the usual crude cell extract assay because of the low-level expression of the gene in *E. coli*. However, genes from Nocardia and Streptomyces can often be expressed to detectable levels when cloned in *Streptomyces lividans*. The cloned fragment containing the methylase gene and possibly the endonuclease gene is subcloned onto a Streptomyces vector such as pIJ486 and transformed into *S. lividans*. The resulting clones in *S. lividans* are examined for methylase and endonuclease gene expression. If there is endonuclease expressed from the clone in *S. lividans*, then endonuclease gene is cloned but not expressed in *E. coli* (skip to step 13). If there is no expression, or if the genes can not be cloned (possibly due to lethality of the genes to be cloned as in the present invention) the NaeI endonuclease is purified as close to homogeneity as possible from *Nocardia aerocolonigenes*, and the amino terminal sequence of the first 20–40 amino acids is determined. This protein sequence information is compared to the translated DNA sequence of the methylase clone to determine if the endonuclease gene is located on that cloned fragment, and if so, where the start of the endonuclease gene is located on that fragment. At the same time, the size of the restriction endonuclease protein is determined by protein gels to be approximately 38 kD. This indicates that the amount of DNA necessary to encode the endonuclease gene is approximately 1.0 kb. Clones carrying the NaeI restriction endonuclease are identified as those that contain the sequence relating to the amino-terminus of the endonuclease and carry at least 1.0 kb of DNA downstream of that sequence.

13. Overexpression: There are a number of ways in which the clone containing the restriction gene can be overexpressed. Sequencing the DNA of the region, and detailed mapping and deletion data help determine the best approach for overexpression of the restriction endonuclease gene. One approach for overexpression comprises inserting a promoter recognized strongly by *E. coli*, such as $P_{tac}$ on pAGR3 (constructed by W. Jack at New England Biolabs) directly in front of the beginning of the restriction endonuclease gene. This may be accomplished by finding convenient restriction targets near the beginning and end of the restriction endonuclease gene and compatible restriction targets near the promoter of pAGR3, and transferring the restriction gene into pAGR3 in line with the $P_{tac}$ promoter. Other strong promoters which can be used are pL on pUC19 and a T7 promoter on the pET3A vector (from William Studier, Brookhaven National Lab., Upton, N.Y.). In addition, a strong ribosome binding site (Shine & Dalgarno 1974 Proc. Natl. Acad. Sci. USA 71, 1342–1346) can be placed in front of the gene to increase expression. In accordance with the present invention, to obtain a stable clone which overexpresses the endonuclease the host has to be pre-protected from endonuclease digestion. This is accomplished by either, cloning in the NaeI methylase on a separate plasmid, (as was done in the present invention to clone the NaeI restriction-modification system in *S. lividans*) or by using a heterologous methylase such as MspI which protects from NaeI digestion by modifying sites which overlap NaeI restriction sites.

The DNA sequence of the gene can be altered by site-directed mutagenesis or by resynthesizing the gene itself to use codons that are more efficiently utilized in *E. coli*.

Primers can be designed that hybridize directly in front of the restriction endonuclease gene and somewhere downstream of the restriction endonuclease gene in order to use the polymerase-chain reaction to amplify the entire restriction endonuclease gene. The resulting DNA fragment can be inserted into an expression vector such as pAGR3.

14. Production: The NaeI methylase or endonuclease may be produced from clones carrying the NaeI methylase gene (or a heterologous methylase) and the overexpressed restriction endonuclease gene by propagation in a fermenter in a rich medium containing ampicillin. The cells are thereafter harvested by centrifugation and disrupted by sonication to produce a crude cell extract containing NaeI methylase and restriction endonuclease activity.

15. Purification: The crude cell extract containing the NaeI methylase and endonuclease is purified by standard protein purification techniques such as affinity-chromatography, or ion-exchange chromatography.

Although the above-outlined steps represent the preferred mode for practicing the present invention, it will be apparent to those skilled in the art that the above described approach can vary in accordance with techniques known in the art.

The following example is given to illustrate embodiments of the present invention as it is presently preferred to practice. It will be understood that this example is illustrative, and that the invention is not to be considered as restricted thereto except as indicated in the appended claims.

EXAMPLE I

Cloning of Nae I Modification Methylase and Restriction Endonuclease Genes

1. DNA purification: To prepare the DNA of *Nocardia aerocolonigenes*, 1 g of cell paste was resuspended by shaking gently for 30 min in 5 ml of 0.1M Tris-HCl, 0.1M EDTA pH 7.6. The suspension was divided into two 3.0 ml portions. 3.5 ml of 1.7 mg/ml lysozyme in 0.1M Tris-HCl, 0.1M EDTA pH 7.6 was added to each portion and each was incubated for 15 minutes at 37° C. SDS was added to 1%, and proteinase K was added to 0.13 mg/ml and then the portions were incubated for 1 hour at 37° C. 0.4 ml of a solution of 10% SDS and 8% sarcosyl was added to each and incubation was continued at 55° C. for 2 hours. The two portions were then combined and dialyzed against four changes of DNA buffer (10 mM Tris-HCl, 1 mM EDTA pH 8.0) for 24 hours. The dialyzed DNA solution was then prepared for cesium chloride-ethidium bromide equilibrium density centrifugation by increasing the total volume to 40 ml with DNA buffer, and then dividing the DNA solution into two 20 ml portions, to each of which 20 grams of cesium chloride and 0.2 ml of 5 mg/ml ethidium bromide were added. The DNA solution was centrifuged at 44,000 rpm for 48 hours and the resulting band of DNA was removed with a syringe and an 18 gauge needle. The ethidium bromide was removed by extracting 4 times with an equal volume of ice-cold, water-saturated N-butanol. The cesium chloride was removed by dialysis. The DNA was then precipitated by adding NaCl to 0.5M and layering 0.55 volume isopropyl alcohol on top. The precipitated DNA was spooled onto a glass rod. The DNA was dissolved in 2 ml 10 mM Tris, 1 mM EDTA pH 8.0 to a final concentration of approximately 385 µg/ml.

NOTE FOR STEPS 2-10: As noted above, a total of 4 different restriction endonucleases were each used to digest the *N. aerocolonigenes* chromosome to construct and screen 9 libraries. Since the methylase gene did not express well enough to survive selection in all cases except PstI, only the details for the PstI library will be provided. The other 13 libraries were prepared by methods similar to those outlined below.

2. Partial digestion: The purified DNA was cleaved with PstI to achieve partial digestion as follows: 115 ul of DNA at 385 ug/ml in 10 mM Tris pH 7.5, 10 mM MgCl$_2$, 50 mM NaCl, 10 mM β-mercaptoethanol buffer was divided into one 100 ul aliquot and five, 50 ul aliquots. To the 100 ul tube was added 10 units of PstI to achieve 1 unit of enzyme per ug of DNA. 50 ul was withdrawn from the first tube and transferred to the second tube to achieve 0.5 units PstI/ug, and so on, each succeeding tube receiving half of the previous amount of PstI. The tubes were incubated at 37° C. for one hour, then heat-treated at 72° C. for 15 minutes and 15 ul from each was analyzed by agarose gel electrophoresis. Tubes exhibiting moderate, but incomplete digestion were chosen as the source of partial digest fragments for cloning. (The partial digestion tubes used were the 0.25 U/ug, 0.12 U/ug, 0.06 U/ug and 0.03 U/ug tubes) The seperate reactions were mixed together and used as described in step 3 below.)

3. Ligation: The fragmented DNA was ligated to pBR322 as follows: 6 ug of PstI-partially digested *Nocardia aerocolonigenes* DNA (60 ul) was mixed with 3.0 µg of PstI-cleaved and dephosphorylated pBR322 (30 ul). 20 ul of 10X ligation mix (500 mM Tris pH 7.5, 100 mM MgCl$_2$, 100 mM DTT, 5 mM ATP) was added, plus 110.5 ul of sterile distilled water to bring the final volume to 198 ul. 7.5 ul of concentrated T4 DNA ligase ($2 \times 10^6$ U/ml) was added and the mixture was incubated at 16° C. for 4 hours then sterilized by the addition of 10 ul of chloroform. Approximately 125 ul of the ligated DNA was used to transform *E. coli* strain K802 as follows: The DNA was mixed with 1.0 ml of SSC/CaCl$_2$ (50 mM NaCl, 5 mM Na$_3$ Citrate, 67 mM CaCl$_2$) on ice and 2.0 ml of ice-cold competent *E. coli* K802 (hsdR$^-$M$^+$, mcrA$^-$, mcrBC$^-$ ATCC No. 33526) cells were added. After a 5 minute incubation at 42° C., the cells were diluted by the addition of 8 ml of Luria-broth (L-broth) then incubated at 37° C. for 1 hour.

4. Primary Cell Library: The transformed cell culture was briefly centrifuged, the supernatant was discarded and the cells were resuspended in 1.0 ml of L-broth. 200 ul portions were plated onto Luria-agar (L-agar) plates containing 25 ug/ml tetracycline. After overnight incubation at 37° C., the plates were each flooded with 2.5 ml of 10 mM Tris pH 7.5, 10 mM MgCl2 and the transformed colonies were scraped together and pooled to form the primary cell library.

5. Primary Plasmid Library: The primary plasmid library was prepared as follows: 2.5 ml of the primary cell library was inoculated into 500 ml of L-broth containing 10 ug/ml tetracycline. The culture was shaken overnight at 37° C. then centrifuged at 4000 rpm for 5 minutes. The supernatant was discarded and the cell pellet was resuspended in 10 ml of 25% sucrose, 50 mM Tris pH 8.0, at room temperature. 5 ml of 0.25M EDTA pH 8.0, was added, followed by 3 ml of 10 mg/ml lysozyme in 0.25M Tris pH 8.0. The solution was left on ice for 3 hours, then 12 ml of lytic mix (1% Triton X-100, 50 mM Tris pH 8.0, 67 mM EDTA) was forcefully pipetted in, and the cell suspension gently swirled to achieve lysis. After lysis, the mixture was transferred to a 50 ml plastic centrifuge tube and spun at 17k rpm, 4° C. for 45 minutes. The supernatant was removed with a pipette. 20.0 g of solid CsCl was weighed into a 50 ml plastic screw-cap tube and 22.0 g of supernatant was pipetted into the tube and mixed. 1.0 ml of ethidium bromide solution (5 mg/ml ethidium bromide in 10 mM Tris pH 8.0, 1 mM EDTA, 100 mM NaCl) was added to the mixture. The solution was transferred to two ⅝ in.×3 in. polyallomer centrifuge tubes and sealed. These tubes were then spun in a Beckman Ti70 rotor for 42 hours at 44000 rpm, and 17° C. To collect the plasmids, the tops of the tubes were pierced with a scalpel and the lower of the two fluorescent DNA bands was collected by syringe under ultraviolet light. The lower band from both tubes was combined into a screw-top glass tube and the ethidium bromide was removed by extracting four times with an equal volume of water-saturated ice-cold N-butanol.

The extracted solution was transferred to dialysis tubing and dialyzed for 24 hours against 4 changes of DNA buffer. The dialyzed DNA solution was then transferred to a pre-weighed 50 ml sterile centrifuge tube and its volume was measured. 5M NaCl was added to a final concentration of 0.4M, then 2 volumes of isopropanol were added and mixed. The solution was stored overnight at −20° C. to precipitate the DNA. After precipitation, the solution was spun at 15000 rpm, 0° C. for 15 minutes and the supernatant discarded. The tube was left on the bench to air-dry for 15 minutes, then the DNA pellet was dissolved in 500 ul of DNA buffer and stored at −20° C. The DNA concentration of plasmids prepared in this way were found to be 100 to 200 ug/ml.

6. Digestion of Plasmid Pool: The gel-purified primary plasmid pool was digested to destroy non-NaeI methylase clones as follows: The plasmid DNA was diluted to 30 ug/ml in NaeI Buffer (20 mM NaCl, 10 mM Tris pH 8.0, 10 mM MgCl$_2$, 5 mM β-mercaptoethanol) A total of 225 ul was prepared. 8 U/ug NaeI was added and the mixture was incubated at 37° C. for 3 hours.

7. Transformation: A 12.5 ul sample from each tube was used to transform *E. coli* K802. After the 3 minute incubation at 42° C. and 45 minutes of growth in L-broth at 37° C., the cell/DNA mixtures were plated onto L-agar plates containing 25 ug/ml tetracycline. After overnight incubation at 37° C., the plates were examined. Digestion of the plasmid library with NaeI was found to have reduced the number of transformants by a factor of about 10$^3$.

8. Analysis of surviving individuals: 42 of the surviving colonies obtained from section 7 were grown up into 10 ml cultures of L-broth containing tetracycline and the plasmids that they carried were prepared by the following miniprep plasmid purification procedure, adapted from the method of Birnboin and Doly (Nucleic Acids Res. 7: 1513 (1979)).

Miniprep Procedure: Each culture was centrifuged at 8000 rpm for 5 minutes; the supernatant was discarded and the cell pellet was resuspended in 1.0 ml of 25 mM Tris, 10 mM EDTA, 50 mM glucose, pH 8.0, containing 1 mg/ml lysozyme. After 10 minutes at room temperature, 2.0 ml of 0.2M NaOH, 1% SDS was added to each tube and the tubes were shaken to lyse the cells and then placed on ice. Once the solutions had cleared, 1.5 ml of 3M sodium acetate pH 4.8, was added to each and shaken. The precipitates that formed were spun down at 15000 rpm, 4° C. for 10 minutes. Each supernatant was poured into a centrifuge tube containing 3 ml of isopropanol and mixed. After 10 minutes at room temperature, the tubes were spun at 15000 rpm for 10 minutes to pellet the precipitated nucleic acids. The supernatants were discarded and the pellets were air-dried at room temperature for 30 minutes Once dry, the pellets were resuspended in 850 ul of 10 mM Tris, 1 mM EDTA pH 8.0. 75 ul of 5M NaCl was added to each and the solutions were transferred to Eppendorf tubes containing 575 ul of isopropanol, and again precipitated for 10 minutes at room temperature. The tubes were then spun for 45 seconds in a microfuge, the supernatants were discarded and the pellets were air-dried. The pellets were then dissolved in 500 ul of 10 mM Tris pH 8.0, 1 mM EDTA, containing 100 ug/ml RNase and incubated for 1 hour at 37° C. to digest the RNA. The DNA was precipitated once more by the addition of 50 ul of 5M NaCl followed by 350 ul of isopropanol. After 10 minutes at room temperature, the DNA was spun down by centrifugation for 45 seconds, the supernatants were discarded, and the pellets were redissolved in a final solution of 150 ul of mM Tris, 1 mM EDTA pH 8.0. The plasmid minipreps were subsequently analyzed by digestion with NaeI.

9. Methylase Gene Clones: Nineteen plasmids were found to be resistant to NaeI and to carry at least two PstI fragments (FIG. 2). In each case except one, the fragment was in the same orientation with respect to the plasmid's ampicillin resistance gene promoter. The one clone with the insert in the opposite orientation with respect to the ampicillin resistance gene promoter gave only partial protection of the plasmid from NaeI endonuclease digestion. An in vitro restriction assay was performed on extracts prepared from the different *E. coli* clones, as follows:

A 50 ml culture of the clone to be tested for endonuclease activity was grown overnight in L-broth plus 25 ug/ml tetracycline at 37° C. The cells were pelleted by centrifugation at 5000 rpm for 5 minutes. The supernatant was discarded and the pellet was resuspended in 3 ml of sonication buffer (20 mM KPO$_4$ pH 7.4, 10 mM β-mercaptoethanol). Lysozyme was added to the cell suspension to a final concentration of 200 ug/ml. This mixture was kept on ice for 3 hr, then frozen at −20° C. The mixture was thawed on ice and 2 ml of this suspension was mixed with 2 ml sonnication buffer. 0.4 ul of a 25% solution of Triton X-100 was added to the suspension and mixed by pipetting up and down. The disrupted cells were spun for 10 minutes at 5,000 rpm. The supernatant was assayed for restriction endonuclease activity by incubating 7.5 ul of the cell extract with 120 ul of 1X NaeI Buffer, and 50 ug/ml pBR322 DNA (predigested with BstNI) for 2 hr. at 37° C. A 15 ul sample checked by electrophoresis showed no evidence of restriction endonuclease activity.

10. Location of the methylase gene within the 1.45 and 1.65 kb PstI inserts: The NaeI methylase clone was digested with numerous restriction endonucleases to provide a restriction map of the cloned DNA. Using the map, various regions within the insert were deleted to determine the resulting affect upon methylation. The location of the ~1 kb methylase gene within the 3.1 kb insert was then pinpointed, and the length of cloned DNA on either side of the gene was found to be ~0.9 and ~1 kb. The methylase clone might not have enough DNA (~1 kb) on the right side of the methylase gene to encode a linked restriction endonuclease gene, but may have enough room on the left side by using other larger clones which have about 3.9 kb to the left of the methylase gene. However, since the distance between the two genes, the exact size of the genes, and whether or not they were linked was not known, the lack of NaeI endonuclease activity in the clone indicated that the restriction gene was either not present in the clones, or was present but not expressed. In the event that the restriction gene was present and not expressing, the cloned methylase gene with adjacent DNA was subcloned into a Streptomyces vector which was used to transform *Streptomyces lividans* (step 11, 12). In addition, DNA sequencing and protein sequencing of the methylase clones were undertaken to determine whether part, all or none of the restriction gene was present in the clones (steps 18–19). In the event that the entire restriction gene was not present, the cloning of larger regions of DNA adjacent to the methylase gene was achieved as follows in steps 13–17.

11. Subcloning the NaeI methylase clones into *S. lividans:* With the various methylase clones, there was possibly enough DNA cloned on both sides of the methylase gene to encode a restriction endonuclease gene, if it were linked, and depending on the exact location of the methylase gene. However, since none of the clones expressed any restriction endonuclease activity, and with still no proof that the two NaeI restriction-modification genes were linked, it was decided to try to subclone the methylase clones into *S. lividans*, a species more closely related to *N. aerocolonigenes* than *E. coli* [Below is described the cloning of the 6.4 kb EcoRI-HindIII fragment from pEVnaeIM60; a similar subcloning experiment was performed with a 3 kb KpnI fragment isolated from pEVnaeIM59 (se FIG. 2). The results were the same, so for brevity, only the EcoRI-HindIII subcloning will be described in detail here.] 25 ul (1.5 ug) of pEVnaeIM60 (the 8.4 kb partial PstI methylase clone in pBR322, FIG. 2) was digested in 50 ul of 10 mM Tris pH 7.5, 10 mM $MgCl_2$, 100 ug/ml bovine serum albumin, 100 mM NaCl containing 20 U of EcoRI and 20 U of HindIII at 37° C. for 2 hr. The entire volume was electrophoresed in a 0.7% agarose gel for 2 hr. The 7.5 kb EcoRI-HindIII restriction fragment was collected by electrophoresing into DEAE anion exchange paper for 2 hr. The paper was washed two times in 150 ul of a buffer containing 0.1M NaCl, 10 mM Tris pH 8.0, and 1 mM EDTA. Subsequently, the DNA was eluted from the paper by washing the paper four times with 75 ul of a buffer containing 1.0M NaCl, 10 mM Tris pH 8.0 and 1 mM EDTA. The resulting solution containing the DNA fragment was extracted with 300 ul phenol/chloroform followed by extraction with 300 ul chloroform and precipitated with 1 ml absolute ethanol by placing in a dry ice/ethanol bath for 15 min. The DNA was pelleted at 14k rpm for 5 min. The pellet was rinsed with 70% ethanol, air dried and resuspended in a final volume of 10 ul 10 mM Tris pH 8, and 1 mM EDTA. 10 ul (0.5 ug) of the EcoRI-HindIII purified DNA fragment were ligated to 2 ul (0.2 ug) of EcoRI-HindIII cleaved and dephosphorylated pIJ486 (pIJ486 was obtained from Hopwood, D. A. of Norwich, England. pIJ486 is described in the publication, Ward, J. M. et al., Mol. Gen. Genet. 203:468–478.) in a final volume of 50 ul in 1×ligation buffer containing 1 ul T4 DNA ligase (400 U) at 12° C. overnight. 10 ul of the ligation mix was added to approximately $4\times10^9$ *S. lividans* TK24 (obtained from Hopwood, D. A. TK24 is described in Hopwood, D. A., et al., *Genetic Manipulation of Streptomyces, a Laboratory Manual*) protoplasts, prepared as described in Hopwood D. A., et al., ibid, in P Buffer [103 g Sucrose, 0.25 g $K_2SO_4$, 2.02 g $MgCl_2.6H_2O$, 2 ml Trace elements solution, and distilled water to 800 ml. 80 ml aliquots are dispensed and autoclaved. Before using the following is added to each 80 ml: 1 ml 0.5% $KH_2PO_4$, 10 ml 3.68% $CaCl_2.2H_2O$ and 10 ml 5.73% TES buffer pH 7.2. Trace elements solution per liter: 40 mg $ZnCl_2$, 200 mg $FeCl_3.6H_2O$, 10 mg $CuCl_2.4H_2O$, 10 mg $MnCl_2.4H_2O$, 10 mg $Na_2B_4O_7.10H_2O$ and 10 mg $(NH_4)6Mo_7O_{24}.4H_2O$] 0.5 ml of 25% polyethylene glycol 1000 was added to the protoplast/DNA mixture This was drawn up and down 3 times in a 1 ml pipette. 0.1 ml of the transformation mix was plated on each of six R2YE plates [103 g Sucrose, 0.25 g $K_2SO_4$, 10.12 g $MgCl_2.6H_2O$, 10 g glucose, 0.1 g Difco casaminoacids and 800 ml $H_2O$. 80 ml of this solution is mixed with 2.2 g Difco agar and autoclaved. To prepare the plates the base agar solution is melted and the following sterile solutions are added: 1 ml 0.5% $KH_2PO_4$, 8 ml 3.68% $CaCl_2.2H_2O$, 1.5 ml 20% L-proline, 10 ml 5.73% TES buffer pH 7.2, 0.2 ml Trace elements solution, and 0.5 ml 1N NaOH. The plates are poured and dried in a laminar flow hood for at least one hr.]. The plates were overlayed after incubating overnight at 30° C. with 1.0 ml of an aqueous solution of thiostrepton (0.5 mg/ml). The plates were returned to 30° C. for 3 to 4 days until the colonies have grown.

12. Analysis of transformants: the colonies obtained from the thiostrepton selection were streaked on R2YE plates containing 5 ug/ml thiostrepton for isolated colonies. Once grown, these were used to innoculate 5 ml of TSB, Oxoid Tryptone Soya Broth, with 5 ug/ml thiostrepton. These cultures were incubated at 30° C. with aeration for 24 hr. Minipreps were done on 1 ml of the cultures. This procedure is identical to the procedure described by Birnboim and Doly (Nucleic Acids Res. 7:1513 (1979)) with the exception that a 30 minute incubation in 4 mg/ml of lysozyme, 50 mM glucose, 25 mM Tris pH 8.0, and 10 mM EDTA at 37° C. is necessary before adding the NaOH-SDS solution. 10 ul of the miniprep DNA was analyzed by running on an 0.7% agarose gel. 2 of the 5 clones appeared to have the correct sized fragment inserted in pIJ486. Spores from these two isolates were harvested and used to inoculate 500 ml TSB with 5 ug/ml Thiostrepton. CsCl plasmid preps were prepared on the cultures following a scaled up (20X) version of procedure 3, p.93 in Hopwood et al. ibid. The resulting pellet was resuspended in 17 ml 10 mM Tris pH 8.0, 1 mM EDTA, 18.7 g CsCl and 0.44 ml ethidium bromide (5 mg/ml). The solution was transferred to two ⅝ in.×3 in. polyallomer centrifuge tubes and sealed. These tubes were centrifuged in a Beckman Ti70 rotor for 44k rpm for 48 hr, 17° C. To collect the plasmids, the tops of the tubes were pierced with a scalpel and the lower of the two fluorescent DNA bands was collected by syringe under ultraviolet light. The lower band from both tubes was combined into a 15 ml Corex tube and the ethidium bromide was removed by adding an equal volume of water and three volumes of ethanol. After 2 hr at −20° C. the DNA was pelleted by spinning at 12k rpm for 20 min. The pellet was resuspended in 2 ml 10 mM Tris pH 8.0, 1 mM EDTA. 50 ul of 8M LiCl was added and the DNA was extracted with phenol/chloroform followed by a chloroform extraction. The DNA was precipitated by adding 3 volumes ethanol to the aqueous solution as described above. The pellet was resuspended in 500 ul 10 mM Tris pH 8.0, 1 mM EDTA. The purified plasmid was digested with EcoRI and HindIII to confirm the presence of the insert as well as with NaeI to determine if the subclone in *S. lividans* had any NaeI methylase activity. Both subclones were apparently identical having the correct construction as well as having methylase activity i.e., were unable to be digested with the NaeI restriction endonuclease. To test for NaeI restriction endonuclease activity, 50 ml of culture grown identically to that used for the plasmid prep was pelleted. The pellet was washed with 10.3% sucrose and frozen at −70° C. Upon thawing the pellet was resuspended in 3 ml/g of wet cell weight with a solution of 50 mM Tris pH 8.0, 10 mM β-mercaptoethanol and 1 mM PMSF. After sonication on ice the debris were removed by centrifugation at 16k rpm for 45 min. The supernatant was assayed for NaeI restriction endonuclease activity. These subclones, denoted pEGnaeIM1-21, and pEGnaeIM1-22, had no detectable NaeI endonuclease activity in S. lividans.

13. A genomic map of the adjacent regions was determined using the southern blot technique (Southern, E. 1975, J.Mol.Bio., 98:503) and a portion of the methylase clone containing a portion of the methylase gene and DNA to the right of the methylase gene as a probe, specifically, the 1.65 kb fragment (FIG. 2) gel-purified and nick-translated with alpha-$^{32}$P-ATP. The fragment was purified by electrophoresing for four hours in a 1% agarose gel containing 0.01% SDS. Using long-wave Uv to view the gel, the 1.65 kb band was cut from the gel and minced using a clean razor blade. The mixture was forced through a 22-gauge syringe into 5 ml 1X agarose gel buffer containing 0.01% SDS, and centrifuged 17k rpm 45 minutes. The supernatant was precipitated with 0.5 ml 5M NaCl and 1.1 ml n-butanol at −70° C. overnight. The DNA was pelleted 15k rpm, 20 minutes. The pellet was resuspended in 400 ul 10 mM Tris pH 8.0, 1 mM EDTA, phenol/chloroform extracted, chloroform extracted three times and precipitated again with 40 ul 5M NaCl and 1000 ul isopropanol at −20° C. three hours. The pellet was rinsed with 70% isopropanol, air dried, and resuspended in a final volume of 20 ul 10 mM Tris pH 8.0, 1 mM EDTA. The gel-purified probe was nick-translated as follows: 5 ul (0.5 ug) DNA, 1.5 ul buffer (500 mM Tris pH 7.5, 10 mM β-mercaptoethanol, 50 mM MgCl$_2$), 1 ul GTC (500 pmoles/ul), 5 μl alpha-$^{32}$P-dATP (100 pmoles, 800 Curies/millimole), 2 ul DNA polymerase I (20 units), and 1 ul DNAse I (1 ug/ml) were mixed together and incubated 16° C. for 2 hr. The mixture was then boiled for 10 minutes and placed immediately on ice.

The southern blot was prepared as follows: N. aerocolonigenes DNA was digested separately with the restriction endonucleases AatII, BamHI, BclI, EcoRI, HindIII, MluI, NcoI, NdeI, NotI, NsiI, PvuII, SacI, SalI, ScaI, SmaI, SphI, and StuI. The digests were electrophoresed on a 1.0% agarose gel. The gel was soaked in 0.25M HCl for 10 min; 0.4M NaOH, 0.8M NaCl for 30 min; and then in 0.5M Tris pH 7.5, 1.5M NaCl for 30 min. A nitrocellulose sheet was soaked briefly in water, then in 5 X SSC (0.75M NaCl, 75 mM Na$_3$Citrate). The gel was placed on top of a ½ inch stack of chromatography paper (Whatman) in 300 ml 3M NaCl, 0.3M Na$_3$Citrate buffer, with the level of buffer just below the height of the stacked paper. The nitrocellulose sheet was placed on top of the gel and backed with chromatography paper (Whatman) to act as a wick. The sandwich was weighted down and transfer of the gel contents to the nitrocellulose sheet was allowed to proceed at room temperature overnight. The sheet was then rinsed in 0.15M NaCl, 15 mM Na$_3$Citrate for ten minutes and baked in a vacuum oven at 80° C. for 1.5 hr. to fix the transferred DNA fragments to the nitrocellulose. The sheet was transferred to a plastic bag containing 15 ml of a solution composed of 3 ml of 10 g/l Ficoll, 10 g/l polyvinylpyrrolidone, 10 g/l bovine serum albumin; 4.5 ml of 3M NaCl, 0.3M Na$_3$Citrate; 1.5 ml 10% SDS; 3 ml 10% dextran sulfate; 3 ml H$_2$O, and prehybridized by incubating at 65° C. shaking for 3 hr. 7 ul radioactive probe was added to the bag, and incubation was continued at 65° C. shaking overnight. The nitrocellulose sheet was then washed three times for 5 minutes each at room temperature with 0.3M NaCl, 30 mM Na$_3$Citrate; and once for twenty minutes at 65° C. in the same buffer containing 0.5% SDS. The sheet was then air-dried and autoradiographed overnight.

Figure 4:
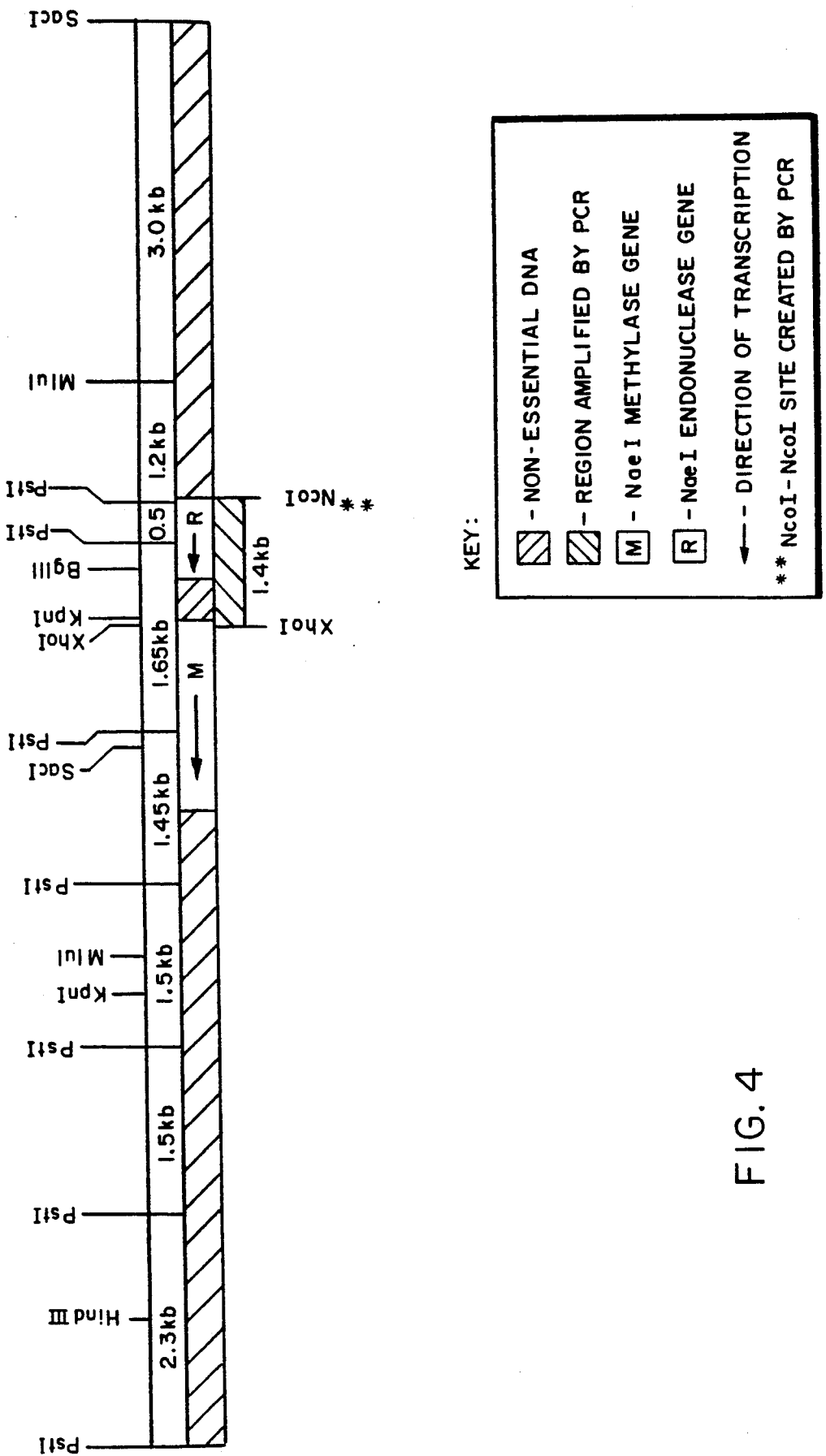
FIG. 4 is a restriction map of the entire 12.8 kb of *Nocardia aerocolonigenes* DNA that has been cloned. The location of the 1.4 kb fragment used to construct pCTnaeIR16-1 is indicated on the diagram. For simplicity, only those restriction sites which are of relevance to this patent are included in this figure.

From the southern blot data, the exact sizes of six endonuclease encoding fragments were known. AatII, BamHI, MluI, PvuII, SacI, SalI fragments carry DNA to the left of the methylase gene; (FIG. 4). The probe hybridized to a single 2.6 kb band in the AatII digest, to a 7.5 kb band in the BamHI digest, to a 4.9 kb band in the MluI digest, to a 2.3 kb band in the PvuII digest, to a 6 kb band in the SacI digest, and to a 2 kb band in the SalI digest. The other bands were judged to be too large to clone.

14. Construction of pEVnaeI7-5: Partial digestion of pEVnaeIM-59 was achieved by mixing 34 ul (30 ug) of pEVnaeIM-59 with 60 ul 10X NEBuffer 3 (50 mM Tris HCl, 10 mM MgCl$_2$, 100 mM NaCl, 1 mM DTT) and bringing up to 600 ul with H$_2$O. 100 ul of the DNA mixture was placed in the first tube, and 50 ul were placed in four additional tubes. 5 U of PstI was mixed into the tube with 100 ul of the DNA mixture. 50 ul was removed from this tube and placed into the first tube with 50 ul, diluting the enzyme 1:1. Successive 1:1 dilutions were done into the three remaining tubes. The reactions were incubated at 37° C. for 1 hour. The reaction was stopped by heating at 72° C. for 15 min. 5 ul from each reaction was electrophoresed in a 0.7% agarose gel to determine the extent of digestion. The remainder of the DNA from the tubes which appeared to give the correct level of digestion were combined and electrophoresed in and agarose gel. The 7 kb band (containing pBR322 and the 1.5 kb and the 1.45 kb fragments from pEVnaeIM-59) was gel purified as described in step 13. 12.5 ul (about 50 ng) of the isolated fragment was ligated to itself by adding 1.5 ul 10X ligase buffer and 1 ul T4 DNA ligase and incubating at 16° C. for 5 hours. 10 ul of the ligation mixture was used to transform competent E. coli RR1. Transformants were selected on L-agar with 25 ug/ml tetracycline. 32 colonies survived the selection. 12 of the surviving colonies were picked for plasmid mini preps. Of the 12 colonies picked, 3 had the correct construction i.e. had pBR322, the 1.5 kb and the 1.45 kb fragments (FIG. 3). The subclones were sensitive to NaeI digestion so were assumed to not contain the intact methylase gene.

15. A SacI library was constructed and selected by the same procedures as steps 2-8 with the following modification at steps 2 & 4: 30 ul (30 ug) N. aerocolonigenes chromosomal DNA was digested completely in 300 ul 1X NEBuffer 2 (10 mM Tris pH 7.5, 10 mM MgCl$_2$, 150 mM NaCl, 1 mM DTT) containing SacI (20 U) at 37° C. for 3 hours. The entire volume was electrophoresed in a 1% agarose gel containing 0.01% SDS for 5 hours. Using long wave Uv to view the gel, the fragments within the size range of the known size of the methylase-gene-carrying fragment were cut out of the gel and minced with a clean razor blade. The fragments were purified following the same procedure as step 13. 15 ul (0.8 ug) was ligated to 2 ul (0.8 ug) of SacI-cleaved and dephosphorylated pEVnaeI7-5 in 70 ul 1X ligation buffer containing 1200 U T4 DNA ligase at 16° C. 4 hours. All 70 ul was transformed into *E. coli* RR1 and K802 and plated on L-agar with tetracycline. After overnight incubation at 37° C., the plates were each flooded with 2.5 ml of 10 mM Tris pH 7.5, 10 mM MgCl2 and the transformed colonies were scraped together and pooled to form the primary cell library. A primary plasmid library was made from the primary cell library as described in step 5.

16. Isolation of a clone carrying the region upstream of the NaeI methylase gene: Since all attempts to isolate the NaeI methylase clone using normal methylase selection of the SacI primary plasmid library (as described in steps 6–7) resulted in no surviving colonies, a less stringent methylase selection of the SacI primary plasmid library was done. In addition, the *E. coli* strain AP1-200 was used as the host. AP1-200 caries a dinD::lacZ fusion which in the presence of other mutations contained in the host can indicate the presence of an active methylase (Piekarowicz, Nucleic Acid Res. 19:1831–1835 (1991)). 2.5 ul of the SacI primary plasmid library (~0.1 ug of DNA) was digested with 0.5 ul of NaeI (2U) in 50 ul of 1X NEBuffer 1 (10 mM Bis Tris propane HCl, 10 mM MgCl2, 1 mM DTT) for 30 min at 37° C. 20 ul of the reaction mix was used to transform competent *E. coli* AP1-200. The cells were plated on L-agar with tetracycline and 40 ug/ml x-gal. The plates were incubated overnight at 43° C., shifted to 30° C. for 3 hours and then shifted back to 43° C. for 2 hours. One colony arose from the library which appeared to be blue, indicating the possible presence of an active methylase. Restriction mapping of the plasmid purified from the SacI clone, named pEVnaeIRM9.3, revealed that a 6.0 kb SacI fragment had been inserted into the cloning vector pEVnaeI7-5 (FIG. 3). This clone was partially protected from NaeI restriction endonuclease digestion. However, no NaeI restriction endonuclease activity was detected from any *E. coli* strains harboring pEVnaeIRM9.3.

17. All attempts to subclone pEVnaeIRM9.3 into *Streptomyces lividans* by cloning the SacI fragment into a Streptomyces vector containing the NaeI methylase or by cloning the MluI fragment containing the NaeI methylase and at least 2.6 kb of DNA upstream of the methylase gene (FIG. 3) into pIJ486 were unsuccessful. Therefore, it was not possible to determine by this method whether the endonuclease gene was present on pEVnaeIRM9.3 but just not expressed at a high enough level to be detected in *E. coli*, or if the endonuclease gene was not linked to the methylase gene and so not cloned.

18. To try to determine if the endonuclease gene was present on the cloned fragments, and if so, where, the NaeI restriction endonuclease was purified as close to homogeneity as possible as follows:

3.3 liters of crude cell extract from 960 g of *Nocardia aerocolonigenes* was placed over the following columns in the following order: DEAE Sepharose, Affi-gel Blue, Heparin-Sepharose, Phosphocellulose, MonoQ FPLC, and Heparin TSK FPLC resulting in ~50% pure NaeI restriction endonuclease preparation.

100 ul (2.5 ug) of the purified NaeI restriction endonuclease was used for amino terminal protein sequencing on Applied Biosystems Model 470A gas phase protein sequencer. The first 21 amino acid residues of the restriction endonuclease were determined (SEQ ID:-NO.2).

19. DNA sequencing of the region confirmed that the restriction gene was present on the SacI clone pEVnaeIRM9.3, that the restriction gene was upstream of the methylase gene, and that it was being transcribed in the same direction as the methylase gene (FIG. 4 and SEQ ID NO:1). The sequence also provided data to use as a basis for subsequent manipulations of the recombinant plasmid to induce expression of the cloned restriction gene in *E. coli.*

Figure 5A:
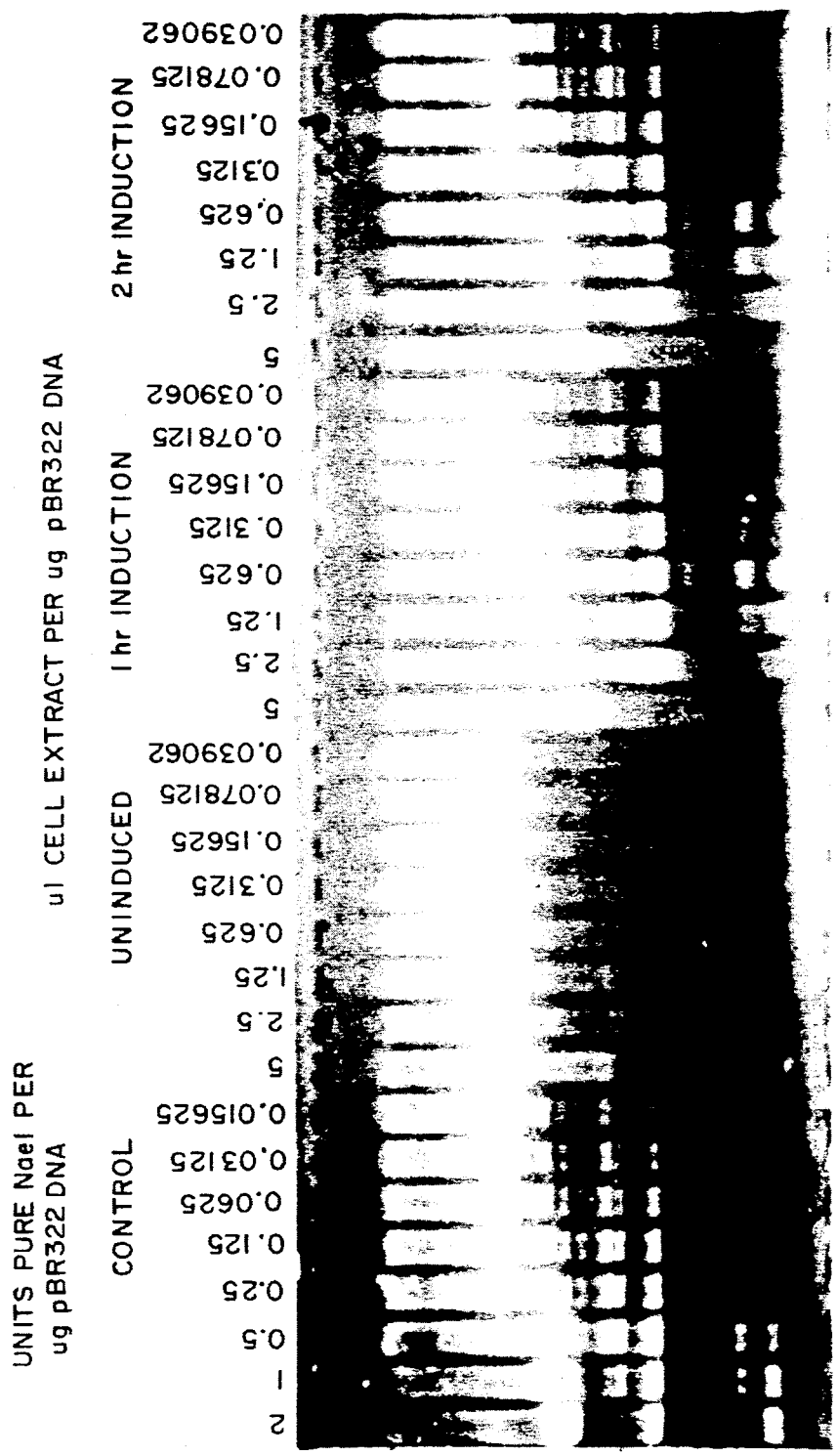
FIGS. 5A and 5B is a photograph of an agarose gel illustrating the induction of NaeI restriction endonuclease activity obtained from the cell extracts of NEB#777.
Figure 5B:
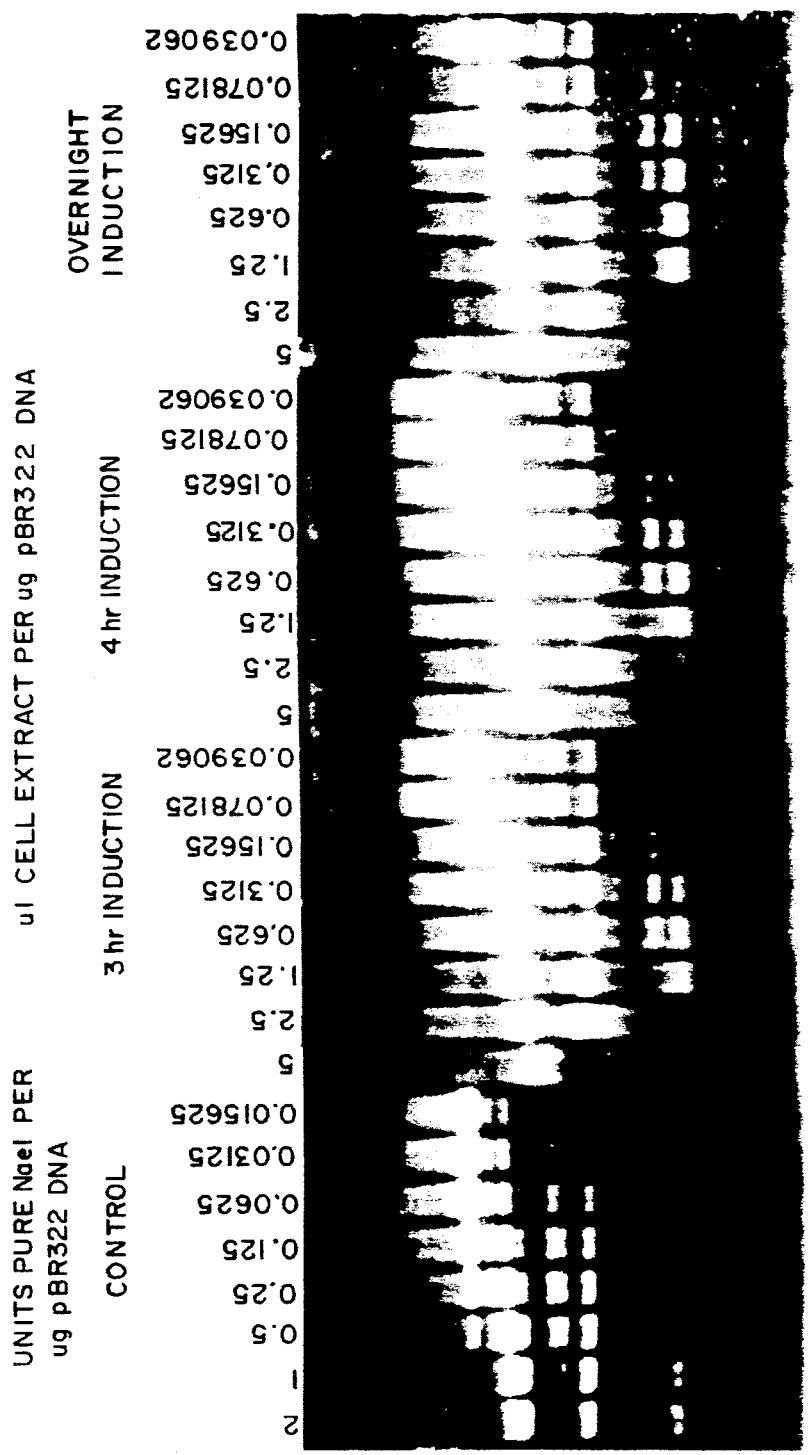

20. Overexpression of NaeI restriction endonuclease: Two oligonucleotide primers were made using the DNA and protein sequence data. One primer, a 24mer, contained the sequence estimated to be about 500 nucleotides downstream of the carboxy terminus of the endonuclease gene, this included an XhoI site found in that sequence (FIG. 4 and SEQ ID NO:1). The other primer, a 27mer, contained the sequence which overlaps the AUG codon, indicated by protein sequencing to be the start of the endonuclease gene, with an added NcoI site which changes the second amino acid of the endonuclease from a threonine to an alanine. These two primers were used with pEGnaeIRM6-1 as a template (an MluI subclone of pEVnaeIRM9.3 in pUC19) in a polymerase chain reaction to generate about a 1.4 kb DNA fragment. This PCR product was digested with XhoI and NcoI in 1X NEBuffer 4 and Purified from and agarose gel using the BioRad Prep-A-Gene kit as per manufacturers instructions. The purified fragment (~0.1 ug) was ligated into the P$_{tac}$ expression vector, pAGR3 (a pBR322 based vector, constructed by W. Jack at New England Biolabs, containing an ampicillin resistance gene, a single copy of lacI$^q$, the P$_{tac}$ promoter, a 4 fold direct repeat of rrn$_b$ terminator upstream of the P$_{tac}$ promoter to prevent read-through transcription, and an NcoI site downstream of a lac ribosome binding site) which had been digested with XhoI and NcoI (~0.05 ug) in a total volume of 40 ul with 400 U of T4 DNA ligase at 37° C. for 2 hours. After drop dialysis, 10 ul of the ligation was used to electroporate *E. coli* K802 which had the MspI methylase gene integrated in the chromosome (the MspI methylation recognition site, CCGG, overlaps the NaeI restriction endonuclease recognition site and so protects the host from NaeI digestion). The electroporated cells were grown for 30 min. at 37° C. and plated on L-agar with ampicillin (100 ug/ml). Over 120 colonies survived the selection, of those, 70 colonies were picked and streaked onto L-agar with ampicillin for isolated colonies. Plasmids were isolated from the individual colonies by picking and resuspending the colony into 25 ul of STET (8% Sucrose, 5% Triton X-100, 50 mM EDTA, and 50 mM Tris-HCl pH 8.0). 25 ul phenol (equilibrated with 0.1M Tris pH 8.0) was added to the STET-cell mixture. The tubes were vortexed and spun in an Eppendorf centrifuge. The supernatant was mixed with 2 ul of loading dye and loaded directly onto a 0.7% agarose gel. 12 of the 70 colonies tested appeared to contain plasmids larger than the vector, pAGR3. These 12 colonies were grown in 10 ml L-broth with ampicillin overnight at 37° C. Mini plasmid preparations were made from these cultures as described in step 8. NcoI and XhoI digests of 10 ul of each miniprep were compared with NcoI and XhoI digests of pAGR3. Of the 12 clones, 7 appeared to have the correct construction. These 7 clones were grown in 500 ml L-broth with ampicillin to a Klett of 60 (mid log phase) and induced with 1 mM IPTG. 50 ml of culture was removed at 0, 1, 2, 3 and 15 (overnight) hours after induction. The cells were harvested by centrifugation, washed once in cold Sonication buffer (50 mM Tris pH 8.0, 10 mM β-mercaptoethanol, 1 mM PMSF and 0.1 mM sodium azide) and the pellet was frozen at −70° C. After 30 min the pellet was thawed on ice, resuspended in 3 ml of Sonication buffer per gram of cells and sonicated on ice. The sonicated cell extract was centrifuged at 16k rpm for 1 hour. 25 ul of 5 successive 1:1 dilutions of the supernatant, the crude cell extract, were mixed with 25 ul of a DNA mixture containing, 12 ul pBR322 (12 ug), 90 ul 10 X NEBuffer 1, 22.5 ul PstI (20 U/ul), brought up to 900 ul with water. The reaction was incubated at 37° C. for 1 hour. The entire 50 ul was run on a 0.7% agarose gel. The titers from the crude cell extracts were compared to the known titer from the purified NaeI restriction endonuclease (FIG. 5). 3 of the 7 clones had little or no detectable NaeI restriction endonuclease activity. However, 4 clones had approximately $7.7 \times 10^4$ U of NaeI restriction endonuclease activity per gram of cells after overnight induction with 1 mM IPTG (FIG. 5). This level is about 50X more NaeI restriction endonuclease activity per gram of cells than is observed in crude extracts of *Nocardia aerocolonigenes*. One of these clones was selected for further characterization and was given a strain designation of NEB# 777, with the plasmid named pCTnaeIR16-1 (ATTC# 68949).

21. The NaeI restriction endonuclease may be produced from NEB# 777 by propagation to mid-log phase in a fermenter in a rich medium containing ampicillin. The culture is then induced with an addition of 1 mM IPTG and allowed to continue growing for approximately 12 hours or overnight. The cells are then harvested by centrifugation.

22. Purification of the NaeI restriction endonuclease from NEB# 777: All further procedures were performed either on ice or at 4° C. 32.22 grams of cells were resuspended in 150 ml of Buffer A (20 mM potassium phosphate pH 6.9, 50 mM NaCl, 0.1 mM EDTA, 1 mM β-mercaptoethanol, 5% glycerol) and sonnicated (Heat Systems-Ultrasonics Cell Disruptor) at setting 9, 50% cycle, for 15 min. The extract was centrifuged at 10k rpm for 20 min at 4° C. and the resulting supernatant was loaded onto a column of DEAE Sepharose CL-6B (2.6×14 cm) equilibrated with Buffer A. The flow-through was collected and immediately applied to a column of Heparin Sepharose CL-6B (1.6×13 cm) equilibrated with Buffer A. The column was washed with 80 ml of Buffer A, followed by a linear gradient of sodium chloride formed with 125 ml of Buffer A and 125 ml of Buffer A containing 1M NaCl. Fractions (2 ml) were collected at a flow rate of 2 ml/min. The peak of enzyme activity was pooled and eluted from the column between 0.5–0.65M NaCl. After dialysis against Buffer A overnight, the pooled enzyme was loaded onto a Mono S HR 5/5 (1 ml) column equilibrated with Buffer B (20 mM potassium phosphate pH 6.9, 50 mM NaCl, 1 mM β-mercaptoethanol, 5% glycerol). The flow-through was collected and immediately applied to a Mono Q HR 5/5 (1 ml) column also equilibrated with Buffer B. Again the flow-through was collected and then loaded onto a column of DNA Cellulose (0.5×5 cm) equilibrated with Buffer B. The column was washed with 2 ml of Buffer B before a linear gradient of sodium chloride formed with 25 ml of Buffer B and 25 ml of Buffer B containing 0.6M NaCl was applied. 1 ml fractions were collected at a flow rate of 0.15 ml/min. The peak of enzyme activity eluted between 0.17–0.24M NaCl. Fractions containing activity were pooled and concentrated by dialyzing against Buffer C (10 mM Tris pH 7.4, 50 mM sodium chloride, 0.1 mM EDTA, 1 mM DTT, 50% glycerol. This purification scheme produced 384,000 total units of enzyme, a 16% yield and appeared by SDS-PAGE to be about 95% pure.

The NaeI restriction endonuclease obtained from this purification was substantially pure and free of non-specific endonuclease and exonuclease. The purity of the NaeI restriction endonuclease preparation was checked by looking at the following criteria: 1) Ligation: After a 10-fold overdigestion of Adeno-2 DNA, greater than 90% of the DNA fragments produced were ligated with T4 DNA Ligase (at a 5' termini concentration of 1-2 uM at 16° C.). Of these ligated fragments, 95% were able to be recut. 2) Prolonged digestion: After incubating a 50 ul reaction containing 1 ug of Adeno-2 DNA and 50 units of enzyme for 16 hours, the same pattern of DNA bands was produced as a reaction performed in one hour with one unit of enzyme. 3) Exonuclease Activity: After incubation of 60 units of enzyme for 4 hours at 37° C. in a 50 ul reaction containing 1 ug sonnicated $^3$H DNA ($10^5$ cpm/ug) less than 0.07% radioactivity was released. 4) Endonuclease Contamination: After incubation of 60 units of enzyme for 4 hours at 37° C. in a 50 ul reaction containing 1 ug φX174 RFI DNA, less than 5% was converted to RF II. All tests were performed in the following reaction buffer: 10 mM Bis Tris Propane-HCl pH 7.0, 10 mM MgCl$_2$, 1 mM DTT.

NOTE: To enable the cloning of the NaeI restriction endonuclease gene H directly downstream of the P$_{tac}$ promoter in pAGR3 (in example 1, step 20), the sequence of the restriction endonuclease gene was changed using primers and PCR to create an NcoI site. This DNA sequence change of one base pair resulted in the second amino acid of the NaeI restriction endonuclease produced from the resulting clone, to be changed from a threonine to an alanine. All functional assays of this recombinant restriction endonuclease indicated that it had the same specificity and properties as the NaeI restriction endonuclease isolated from *Nocardia aerocolonigenes*. In order to change the second amino acid in the recombinant NaeI restriction endonuclease was changed back to a threonine. An experiment identical to experiment 1 step 20 can be performed with an oligonucleotide which contains a BspHI site in place of the NcoI site. The BspHI site while overlapping the AUG start codon of the restriction endonuclease gene does not change the second codon unlike using the NcoI site. Using this newly constructed oligonucleotide in conjunction with another newly constructed oligonucleotide spanning the BglII site within the restriction endonuclease gene (FIG. 4 and SEQ ID NO:1), a 0.55 kb DNA fragment can be obtained by polymerase chain reaction. The resulting fragment can be digested with BspHI and BglII to give sticky ends for cloning. This fragment containing the corrected amino-terminus of the restriction endonuclease gene can be ligated into the large BglII-NcoI fragment of pCTnaeIR16-1 which contains the vector and the carboxy portion of the restriction endonuclease gene. The ligation mixture can be electroporated into the *E. coli* host strain which contains the MspI methylase gene integrated on the chromosome. This should yield a NaeI restriction endonuclease which contains a threonine as the second amino acid.

---

What is claimed is:

1. Isolated DNA coding for NaeI restriction endonuclease, wherein the isolated DNA is obtainable from the plasmid pCTnaeIR16-1.

2. A recombinant vector comprising a vector into which DNA coding for NaeI restriction endonuclease has been inserted.

3. A recombinant vector comprising the isolated DNA of claim 1.

4. The recombinant vector of claim 3, wherein the vector comprises the plasmid pCTnaeIR16-1.

5. A host cell transformed with the recombinant vector of claim 2, 3 or 4.

6. A method of producing NaeI restriction endonuclease comprising culturing a host cell transformed with the vector of claim 2, 3 or 4 under conditions suitable for expression of said endonuclease.

7. The isolated DNA of claim 1, wherein the isolated DNA comprises SEQ ID NO:1.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 3664 base pairs
        ( B ) TYPE: nucleic acid
        ( C ) STRANDEDNESS: double
        ( D ) TOPOLOGY: linear ( i x ) FEATURE:
        ( A ) NAME/KEY: CDS
        ( B ) LOCATION: 146..1099

( x i ) SEQUENCE DESCRIPTION: SEQ ID NO:1:

```
GGTACCGGCA  TCACCATGGG  CCGGAGTTTC  TCGCTCATGG  CCTGCGCGGA  CAACTTCACA          60

CCCATGCCTT  GAGTGCTTCG  AGCACAGAAT  GGAGCGTGTC  ATTGGGGGCA  GCCCATGCCA         120

AGATCATCAG  ATTTGAAGGG  GTCAC ATG ACT GAG TTG CCG CTG CAG TTC GCG             172
                             Met Thr Glu Leu Pro Leu Gln Phe Ala
                              1               5

GAA CCC GAT GAC GAT CTC GAG CGG GTT CGG GCA ACG TTG TAC AGC CTT               220
Glu Pro Asp Asp Asp Leu Glu Arg Val Arg Ala Thr Leu Tyr Ser Leu
 10              15                  20                  25

GAC CCA GAC GGT GAC CGG ACT GCT GGT GTG TTG AGA GAC ACG CTC GAC               268
Asp Pro Asp Gly Asp Arg Thr Ala Gly Val Leu Arg Asp Thr Leu Asp
                 30                  35                  40

CAG TTG TAC GAC GGT CAG CGA ACC GGG AGG TGG AAC TTC GAT CAG CTG               316
Gln Leu Tyr Asp Gly Gln Arg Thr Gly Arg Trp Asn Phe Asp Gln Leu
             45                  50                  55

CAC AAG ACC GAG AAG ACG CAC ATG GGA ACC CTG GTG GAG ATC AAC CTG               364
His Lys Thr Glu Lys Thr His Met Gly Thr Leu Val Glu Ile Asn Leu
         60                  65                  70

CAC CGT GAG TTC CAG TTC GGT GAC GGC TTT GAG ACC GAT TAC GAG ATT               412
His Arg Glu Phe Gln Phe Gly Asp Gly Phe Glu Thr Asp Tyr Glu Ile
     75                  80                  85

GCA GGA GTG CAG GTC GAC TGC AAG TTT TCG ATG AGC CAG GGC GCT TGG               460
Ala Gly Val Gln Val Asp Cys Lys Phe Ser Met Ser Gln Gly Ala Trp
 90                  95                 100                 105

ATG CTG CCT CCG GAG TCG ATC GGG CAC ATC TGT CTG GTC ATC TGG GCA               508
Met Leu Pro Pro Glu Ser Ile Gly His Ile Cys Leu Val Ile Trp Ala
                110                 115                 120

AGT GAT CAG CAG TGC GCA TGG ACC GCA GGA CTG GTG AAG GTC ATA CCC               556
Ser Asp Gln Gln Cys Ala Trp Thr Ala Gly Leu Val Lys Val Ile Pro
            125                 130                 135

CAG TTC CTC GGC ACT GCC AAC CGT GAC CTC AAG CGG CGA CTC ACA CCC               604
Gln Phe Leu Gly Thr Ala Asn Arg Asp Leu Lys Arg Arg Leu Thr Pro
        140                 145                 150

GAA GGC CGT GCC CAA GTT GTC AAA CTG TGG CCA GAT CAC GGA AAG CTG               652
Glu Gly Arg Ala Gln Val Val Lys Leu Trp Pro Asp His Gly Lys Leu
    155                 160                 165

CAG GAG AAC CTG CTC CTG CAC ATC CCC GGT GAC GTG CGC GAT CAG ATC               700
Gln Glu Asn Leu Leu Leu His Ile Pro Gly Asp Val Arg Asp Gln Ile
170                 175                 180                 185

TTC TCA GCG AAA TCC AGC CGC GGT AAT CAG CAC GGT CAG GCG CGC GTG               748
Phe Ser Ala Lys Ser Ser Arg Gly Asn Gln His Gly Gln Ala Arg Val
                190                 195                 200

AAC GAA CTG TTC CGC CGA GTG CAC GGG CGT CTC ATC GGG AGA GCG GTC               796
```

```
Asn Glu Leu Phe Arg Arg Val His Gly Arg Leu Ile Gly Arg Ala Val
        205                 210                 215

ATA GCG ACT GTG GCG CAG CAG GAC GAC TTC ATG AAG CGC GTA CGC GGG        844
Ile Ala Thr Val Ala Gln Gln Asp Asp Phe Met Lys Arg Val Arg Gly
        220                 225                 230

TCA GGC GGC GCG CGT TCG ATC CTT CGG CCT GAA GGA ATC ATC ATT CTT        892
Ser Gly Gly Ala Arg Ser Ile Leu Arg Pro Glu Gly Ile Ile Ile Leu
        235                 240                 245

GGG CAT CAG GAC AAC GAT CCG AAG GTG GCG AAC GAT CTC GGG TTG CCG        940
Gly His Gln Asp Asn Asp Pro Lys Val Ala Asn Asp Leu Gly Leu Pro
250                 255                 260                 265

GTG CCG CGC AAG GGG CAG GTC GTC GCA GCA CGA GTG GTA CCG GCT GAC        988
Val Pro Arg Lys Gly Gln Val Val Ala Ala Arg Val Val Pro Ala Asp
                270                 275                 280

GAG GGA GAC CAG CGG CAA ACC GCT GAG ATC CAG GGG CGG CGC TGG GCC       1036
Glu Gly Asp Gln Arg Gln Thr Ala Glu Ile Gln Gly Arg Arg Trp Ala
            285                 290                 295

GTA GCC GTG CCT GGC GAC CCC ATC GTC GAG GCG CCG GTT GTG CCC CGG       1084
Val Ala Val Pro Gly Asp Pro Ile Val Glu Ala Pro Val Val Pro Arg
        300                 305                 310

AAA TCA GCC GAG TAGGGCGTGG CGCGTCCAGA CTCCGGGAAT TGTCAGTCCT            1136
Lys Ser Ala Glu
        315
```

| | | | | |
|---|---|---|---|---|
| CCGCACTAGT | GTCGAACCCA | TGTTCGAGAT | GATGAAGGGT | GTCCACGACG GCTGCTACCG | 1196 |
| CGTCTTGCAG | CTCTTCGTGC | TCCCAAACCC | GCAACACCCT | CCACCCGGCG TTGGTGAGGG | 1256 |
| ACTGGTTGAC | CGTTCGATCG | CGCTCGACGT | TCCGCCTGAG | CTTCGGCGAC CAGTACCACT | 1316 |
| CGTTCGTCGT | AGGCTGTCGT | CCGTGGTCTG | GGCACACATG | CCAGAAGCAG CCGTCGATGA | 1376 |
| AGACAGCGAC | CTTCCGGGCG | GTGAAGACGA | TGTCGGGTTT | GACCTTGACG CCGTCGCCAA | 1436 |
| GGCGCAGCAG | GAAATCCTTG | CGATACCTGT | ACCCGAGCTT | GAAGAGCGCG CTTCGCAGTG | 1496 |
| CAGCCTCGGG | TTTCGTACCA | CTGCGCCGGT | TCGCCTGCAT | GTTCCGCGAG CGCCCAGCGT | 1556 |
| TCAGCGGCGC | TGGGTAGGTA | CCGCTCGCGT | GTGCTCGAGC | GCGGGCGCAG CTCTGCTGCT | 1616 |
| CTTATCAGAC | ATGCGCGAAA | GCCTCTTGTG | CCGGTTGGCT | ACAGGTACGG GGCGCCGGTG | 1676 |
| GACGATACTG | CATCGCGAGG | TACACCTGAT | CACATTTGGA | CGCGAAAGGG CGCTTGTGC  | 1736 |
| AGAGTCTCGA | GGTAGTGGAG | ATCTGCGCCG | GTGCCGGTGG | TCAGGCGCTG GGCTTGAGA  | 1796 |
| AAGCTGGCTT | CAGTCATCGG | CTTGCCGTTG | AGCTGGACGT | GAACGCGGCA GCGACGCTGC | 1856 |
| GCAAGAACCT | CAAGTCGGAC | GTGGTGATCA | CTGGCGACGT | CGCTGATCCT TCCGTGCTGA | 1916 |
| ACCCGATGGA | ACACCTGGGG | GTGTCGTTGC | TGGCTGGTGG | TGTGCCTTGT CCCCCATTCA | 1976 |
| GCATCGCGGG | CAAGCAGCTC | GGTGCCGACG | ACATGCGGGA | CCTGTTCGCC TGGGCGGTTG | 2036 |
| AGCTGTGCGA | TGTCATGAAG | CCGCGCGCCT | TGATGCTCGA | AACGTCCGT GGCCTCAGTA   | 2096 |
| TGCCCAGGTT | CGCCGGCTAC | CGGCAGCACG | TCCTCGATCG | GCTGAACGAC ATGGGTTACG | 2156 |
| TCGCTGAGTG | GCGTCTCCTG | CACGCATCGG | ACTTTGGGGT | TCCTCAACTC CGGCCGCGTT | 2216 |
| TCGTACTTGT | CGCTCTGCAG | AACAAGTTCG | CCCCCTATTT | CACCTGGCCT GAGCCGACCG | 2276 |
| GTGCGGCACC | CACGGTGGGG | GAGACGTTGA | AGGACCTCAT | GGCCGCGGAC GGCTGGGAAG | 2336 |
| GTGCCGAAGA | GTGGGCGGCT | CAGGCGAACG | ACATCGCACC | AACCATCGTG GGTGGCTCCA | 2396 |
| AGAAACATGG | CGGAGCTGAC | CTCGGCCCGA | CTCGCGCGAA | GCGGGCGTGG GCAGAGCTCG | 2456 |
| GTGTCGACGC | AATGGGAGTC | GCTGACGCGC | CGCCCAGCC  | TGGCGACAAG TTCAAGGTAG | 2516 |
| GACCGAAGCT | GACCTGCGAG | ATGGTTGCCA | GGATCCAAGG | GTGGCGCGAC GGCGAGTGGA | 2576 |
| TCTTCGAGGG | TCGTAAGACC | TCGCGATACC | GCCAGATCGG | TAACGCTTTC CCGCCACCCG | 2636 |
| TGGCTGAAGC | GATCGGCAAG | CGCATCCGTG | CTGCCTTGAA | CATGGAGGGT GAGGGCAGGG | 2696 |

-continued

```
ATCGGGCGGT CGACAGCGAC CACAACCCGT TGTACCGGGC GCTGAAGGAG TCGGGCGATT    2756
TCATGACTCA CCGGCAGCTG GAAAGGGCTG TCGGTCGACC CATCGAGGCA TATGAGCTGG    2816
AGCGCACGAT CTCTGATCTG GGGCGTGACT TCGAGGTCGA GACGAAGGAC GGTGCTTCGG    2876
CGATGGCGTA CAAACTGGGG CCGTTCAAGG CCTTCACAGG CCAAGAGGGT CATTTGCGGC    2936
ACGAGATGTT CGTGCGCCAC CGCACAAAGA TCAGCTAGGA GGAAGGCTGG ATGTCCACAT    2996
AGGCAAAGTG CCCGGCTAAG GTGGACATCC GGCTCAGCAT CAGTCGTCGT CCCCGACGAT    3056
GGCGATGAGG TCTTTTTTCG ACATCGCGAC GTACTTCTTC CTCTTCGCGG TGTTCCGGAT    3116
GATCGCAGGG ATCAGCTCGT AGGTCAGATC GAGTGATCCG AGCACGTAGT AGTCGATGTC    3176
GTTTGACTCG AGGCTCACAA TATCCATGCC CAGTTCGCGC AACTCTCGCA GGCGGCGCTC    3236
GGTGTGGACG GAGTCGGCGG TCACGACCCT GAGCAGGGCT GCCTCCACGT TCTGGCCTTT    3296
GCGTTGCAAA AGCAGGCTGA ACAACTCCTC GTGCACACGG CTCCCATAGG AACGGCGAG    3356
ATAGGCCGCA GGAACGGTGC CACCGTACCG TCGCTCCATT TCAGTGCCGA GTTGGGCGCG    3416
CAGCTCATGA AACTCTTCGC ACCGCTCCGG AAGCCCAGC CGTACGTAAG CCTGCATGGA     3476
CTCAGCGAGG AGCCGCTTAG CGTACAAATA GGTGTCGAGC AGGTCCTGAC TGGAGGTTCC    3536
GCTCCGAAGC TGGACCAGCA GATCTTCGGT TGCGGCCGCT GTATCGGGCC TCAACCGGCT    3596
CCAGTCACCC TGCGGATACC GAGATGCGGT CAAGCTATTT CCCCTTCTGC TTCAGCTGGT    3656
TACTGCAG                                                            3664
```

( 2 ) INFORMATION FOR SEQ ID NO:2:

( i ) SEQUENCE CHARACTERISTICS:
        ( A ) LENGTH: 317 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Thr Glu Leu Pro Leu Gln Phe Ala Glu Pro Asp Asp Asp Leu Glu
 1               5                  10                  15

Arg Val Arg Ala Thr Leu Tyr Ser Leu Asp Pro Asp Gly Asp Arg Thr
                20                  25                  30

Ala Gly Val Leu Arg Asp Thr Leu Asp Gln Leu Tyr Asp Gly Gln Arg
            35                  40                  45

Thr Gly Arg Trp Asn Phe Asp Gln Leu His Lys Thr Glu Lys Thr His
        50                  55                  60

Met Gly Thr Leu Val Glu Ile Asn Leu His Arg Glu Phe Gln Phe Gly
 65                  70                  75                  80

Asp Gly Phe Glu Thr Asp Tyr Glu Ile Ala Gly Val Gln Val Asp Cys
                85                  90                  95

Lys Phe Ser Met Ser Gln Gly Ala Trp Met Leu Pro Pro Glu Ser Ile
               100                 105                 110

Gly His Ile Cys Leu Val Ile Trp Ala Ser Asp Gln Gln Cys Ala Trp
           115                 120                 125

Thr Ala Gly Leu Val Lys Val Ile Pro Gln Phe Leu Gly Thr Ala Asn
       130                 135                 140

Arg Asp Leu Lys Arg Arg Leu Thr Pro Glu Gly Arg Ala Gln Val Val
145                 150                 155                 160

Lys Leu Trp Pro Asp His Gly Lys Leu Gln Glu Asn Leu Leu Leu His
                165                 170                 175

Ile Pro Gly Asp Val Arg Asp Gln Ile Phe Ser Ala Lys Ser Ser Arg
            180                 185                 190
```

Gly Asn Gln His Gly Gln Ala Arg Val Asn Glu Leu Phe Arg Arg Val
    195                 200                 205

His Gly Arg Leu Ile Gly Arg Ala Val Ile Ala Thr Val Ala Gln Gln
    210                 215                 220

Asp Asp Phe Met Lys Arg Val Arg Gly Ser Gly Gly Ala Arg Ser Ile
225                 230                 235                 240

Leu Arg Pro Glu Gly Ile Ile Ile Leu Gly His Gln Asp Asn Asp Pro
                245                 250                 255

Lys Val Ala Asn Asp Leu Gly Leu Pro Val Pro Arg Lys Gly Gln Val
            260                 265                 270

Val Ala Ala Arg Val Val Pro Ala Asp Glu Gly Asp Gln Arg Gln Thr
        275                 280                 285

Ala Glu Ile Gln Gly Arg Arg Trp Ala Val Ala Val Pro Gly Asp Pro
    290                 295                 300

Ile Val Glu Ala Pro Val Val Pro Arg Lys Ser Ala Glu
305                 310                 315